US012116424B2

(12) United States Patent
West et al.

(10) Patent No.: US 12,116,424 B2
(45) Date of Patent: Oct. 15, 2024

(54) COMPOUNDS AND COMPOSITIONS FOR MODULATING LISTERIA VIRULENCE

(71) Applicant: Wisconsin Alumni Research Foundation, Madison, WI (US)

(72) Inventors: Korbin Hong James West, Madison, WI (US); Helen Elizabeth Blackwell, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 17/701,561

(22) Filed: Mar. 22, 2022

(65) Prior Publication Data

US 2022/0298208 A1 Sep. 22, 2022

Related U.S. Application Data

(60) Provisional application No. 63/164,154, filed on Mar. 22, 2021.

(51) Int. Cl.
| | | |
|---|---|---|
| C07K 7/54 | (2006.01) | |
| A01N 63/50 | (2020.01) | |
| A01P 1/00 | (2006.01) | |
| A61K 38/00 | (2006.01) | |
| A61P 31/04 | (2006.01) | |

(52) U.S. Cl.
CPC ............ *C07K 7/54* (2013.01); *A01N 63/50* (2020.01); *A01P 1/00* (2021.08); *A61P 31/04* (2018.01); *A61K 38/00* (2013.01)

(58) Field of Classification Search
None
See application file for complete search history.

(56) References Cited

PUBLICATIONS

Zetzmann et al. (Front Microbiol. 2016; 7:989) (Year: 2016).*
Tal-Gan et al. (J. Am. Chem. Soc. 2013, 135, 7869-7882) (Year: 2013).*
Autret, et al., "Identification of the agr locus of Listeria monocytogenes: role in bacterial virulence," Infect Immun 71(8): 4463-71 (2003).
Blanco-Canosa, et al., "An efficient Fmoc-SPPS approach for the generation of thioester peptide precursors for use in native chemical ligation," Angew Chem Int Ed Engl 47(36):6851-5 (2008).
Brown, et al., "Novel Peptide from Commensal *Staphylococcus simulans* Blocks Methicillin-Resistant *Staphylococcus aureus* Quorum Sensing and Protects Host Skin from Damage," Antimicrob Agents Chemother 64(6)e00172-20 (2020).
Camilli, et al., "Bacterial small-molecule signaling pathways," Science 311(5764):1113-6 (2006).
Chan, et al., "Virulence regulation and quorum sensing in staphylococcal infections: competitive AgrC antagonists as quorum sensing inhibitors," J Med Chem 47(19):4633-41 (2004).
Chaudhuri, et al., "The Listeria monocytogenes ChiA chitinase enhances virulence through suppression of host innate immunity," mBio 4(2):e00617-12 (2013).
De las Heras, et al., "Regulation of Listeria virulence: PrfA master and commander," Curr Opin Microbiol 14(2):118-27 (2011).
Dickey, et al., "Different drugs for bad bugs: antivirulence strategies in the age of antibiotic resistance," Nat Rev Drug Discov 16(7):457-471 (2017).
Farber, et al., "Listeria monocytogenes, a Food-Borne Pathogen," Microbiol Rev 55(3):476-5 (1991).
Freitag, et al., "Listeria monocytogenes—from saprophyte to intracellular pathogen," Nat Rev Microbiol 7(9):623-8 (2009).
Freitag, et al., "Regulation of the prfA Transcriptional Activator of Listeria monocytogenes: Mult

(56) References Cited

PUBLICATIONS

Palmer, et al., "Attenuation of virulence in pathogenic bacteria using synthetic quorum-sensing modulators under native conditions on plant hosts," ACS Chem Biol 6(12):1348-56 (2011).

Paspaliari, et al., "Chitinase expression in Listeria monocytogenes is positively regulated by the Agr system," PLoS One 9(4):e95385 (2014).

Pinheiro, et al., "MouR controls the expression of the Listeria monocytogenes Agr system and mediates virulence," Nucleic Acids Res 46(18)"9338-9352 (2018).

Radoshevich, et al., "Listeria monocytogenes: towards a complete picture of its physiology and pathogenesis," Nat Rev Microbiol 16(1):32-46 (2018).

Rasko, et al., "Anti-virulence strategies to combat bacteria-mediated disease," Nat Rev Drug Discov 9(2):117-28 (2010).

Riedel, et al., "AgrD-dependent quorum sensing affects biofilm formation, invasion, virulence and global gene expression profiles in Listeria monocytogenes," Mol Microbiol 71(5):1177-89 (2009).

Rieu, A.; Weidmann, S.; Garmyn, D.; Piveteau, P.; Guzzo, J., Agr system of Listeria monocytogenes EGD-e: role in adherence and differential expression pattern. Appl Environ Microbiol 2007, 73 (19), 6125-33.

Rieu, et al., "Listeria monocytogenes EGD-e biofilms: no mushrooms but a network of knitted chains," Appl Environ Microbiol 74(14)"4491-7 (2008).

Rodriguez-Lopez, et al., "Current Knowledge on Listeria monocytogenes Biofilms in Food-Related Environments: Incidence, Resistance to Biocides, Ecology and Biocontrol," Foods 7(6) 19 pages (2018).

Rutherford, et al., "Bacterial quorum sensing: its role in virulence and possibilities for its control," Cold Spring Harb Perspect Med 2(11):a012427 (2012).

Scallan, et al., "Foodborne illness acquired in the United States—major pathogens," Emerg Infect Dis 17(1):7-15 (2011).

Schardt, et al., "Comparison between Listeria sensu stricto and Listeria sensu lato strains identifies novel determinants involved in infection," Sci Rep 7(1):17 (2017).

Tal-Gan, et al., "Characterization of structural elements in native autoinducing peptides and non-native analogues that permit the differential modulation of AgrC-type quorum sensing receptors in Staphylococcus aureus," Org Biomol Chem 14(1):113-21 (2016).

Tal-Gan, et al., "Highly potent inhibitors of quorum sensing in Staphylococcus aureus revealed through a systematic synthetic study of the group-III autoinducing peptide," J Am Chem Soc 135(21):7869-82 (2013).

Tal-Gan, et al., "Highly Stable, Amide-Bridged Autoinducing Peptide Analogues that Strongly Inhibit the AgrC Quorum Sensing Receptor in Staphylococcus aureus," Angew Chem Int Ed Engl 55(31):8913-7 (2016).

Thoendel, et al., "Identification of Staphylococcus aureus AgrD residues required for autoinducing peptide biosynthesis," J Biol Chem 284(33):21828-38 (2009).

Thoendel, et al., "Peptide signaling in the Staphylococci," Chem Rev 111(1):117-51 (2011).

Tilney, et al., "Actin filaments and the growth, movement, and spread of the intracellular bacterial parasite, Listeria monocytogenes," J Cell Biol 109(4 Pt 1):1597-608 (1989).

Todd, et al., "Signal Biosynthesis Inhibition with Ambuic Acid as a Strategy To Target Antibiotic-Resistant Infections," Antimicrob Agents Chemother 61(8):e00263-17 (2017).

Vivant, et al., "Listeria monocytogenes, a down-to-earth pathogen," Front Cell Infect Microbiol 3(87) 10 pages (2013).

Vivant, et al., "Survival of Listeria monocytogenes in Soil Requires AgrA-Mediated Regulation," Appl Environ Microbiol 81(15):5073-84 (2015).

Vivant, et al., "The Agr communication system provides a benefit to the populations of Listeria monocytogenes in soil," Front Cell Infect Microbiol 4(160) 7 pages) (2014).

Wang, et al., "Activation and inhibition of the receptor histidine kinase AgrC occurs through opposite helical transduction motions," Mol Cell 53(6):929-40 (2014).

Wang, et al., "Key driving forces in the biosynthesis of autoinducing peptides required for staphylococcal virulence," Proc Natl Acad Sci USA 112(34):10679-84 (2015).

Wang, et al., "Regulation of Virulence in Staphylococcus aureus: Molecular Mechanisms and Remaining Puzzles," Cell Chem Biol 23(2):214-224 (2016).

Williams, et al., "Quorum sensing between bacterial species on the skin protects against epidermal injury in atopic dermatitis," Sci Transl Med 11(490):eaat8329 (2019).

Wright, et al., "Hydrophobic interactions drive ligand-receptor recognition for activation and inhibition of staphylococcal quorum sensing," Proc Natl Acad Sci USA 101(46):16168-73 (2004).

Yang, et al., "Structure-Function Analyses of a Staphylococcus epidermidis Autoinducing Peptide Reveals Motifs Critical for AgrC-type Receptor Modulation," ACS Chem Biol 11(7):1982-91 (2016).

Zetzmann, et al. "DNase-Sensitive and -Resistant Modes of Biofilm Formation by Listeria monocytogenes," Front Microbiol 6:1428 (2015).

Zetzmann, et al., "Characterization of the biofilm phenotype of a Listeria monocytogenes mutant deficient in agr peptide sensing," Microbiologyopen 8(9):e00826 (2019).

Zetzmann, et al., "Identification of the agr Peptide of Listeria monocytogenes," Front Microbiol 7:989 (2016).

* cited by examiner

COMPOUNDS AND COMPOSITIONS FOR MODULATING LISTERIA VIRULENCE

CROSS-REFERENCE TO RELATED APPLICATION

This application claims the benefit of and priority to U.S. Patent Application No. 63/164,154, filed on Mar. 22, 2021, the contents of which are incorporated herein by reference in their entirety.

GOVERNMENT RIGHTS

This invention was made with government support under 1708714 awarded by the National Science Foundation. The government has certain rights in the invention.

SEQUENCE LISTING

The instant application contains a Sequence Listing which has been submitted electronically in XML file format and is hereby incorporated by reference in its entirety. Said XML copy, created on Aug. 26, 2024, is named 032026-1483_SL.xml and is 8,944 bytes in size.

BACKGROUND

The Gram-positive bacterial species *Listeria monocytogenes* (Lm) is a dangerous food-borne pathogen due to its ability to persist in harsh environments through robust biofilm formation on steel, glass, and plastic surfaces common in the food industry. This feature makes it extremely challenging to eradicate Lm in practice. As a result, Lm accounts for over 10% of all food product recalls in recent years (second to only *Salmonella*). Lm infections exhibit a 20-30% mortality rate and cause nearly one-fifth of food-borne illness-related deaths.

Recent studies have shown an increasingly important role for quorum sensing (QS) in controlling Lm virulence (i.e., the ability to infect). Similar to other Gram-positive bacteria, QS in Lm is mediated by the accessory gene regulator (agr) system, which consists of 4 components, AgrA-D, and a peptide signal.[19-21] The polypeptide AgrD is produced at a basal rate within the cell and consists of an N-terminal amphipathic helix, a signal precursor sequence centered around a conserved cysteine, and a C-terminal recognition domain.[22] AgrB, a membrane-bound peptidase, recognizes and cleaves the C-terminal domain of AgrD, then cyclizes the conserved cysteine of AgrD to the new C-terminus.[23] In a manner still not fully understood, AgrD is further processed and exported from the cell as the mature QS signal known as the autoinducing peptide (AIP). As the bacteria population grows and produces AIP, the extracellular AIP concentration reaches a certain threshold and binds/activates the two-component system formed by AgrC and AgrA. In Lm, this AIP:AgrC binding event induces increased expression of key virulence factors associated with invasion of host cells (internalins, listeriolysin O, phospholipases, etc.) as well as with persistence mechanisms such as adherence and biofilm formation on surfaces.

SUMMARY OF THE PRESENT TECHNOLOGY

The present technology provides compounds and compositions for modulating *Listeria monocytogenes* (Lm) virulence. The compounds may be used to activate or inhibit QS by Lm (e.g., as research tools or therapeutics), to reduce Lm virulence, to inhibit the formation and growth of Lm biofilms on surfaces, and to treat Lm infections. Thus, in one aspect the present technology provides compounds of Formula I:

$$\text{(I)}$$

stereoisomers thereof, and/or salts thereof,
wherein
X is S, O, NH, NR, $CH_2$ or CH, provide that the CH forms a double bond with the adjacent carbon;
Z is $R^T$, $R^T$—C(O), an amino acid residue, or a peptide of 2-10 amino acid residues, wherein Z is optionally attached to a solid substrate;
R is an unsubstituted $C_{1-6}$ alkyl group;
$R^{N1}$, $R^{N2}$, $R^{N3}$, $R^{N4}$, and $R^{N5}$ are each independently H or $CH_3$;
$R^1$ is a substituted or unsubstituted alkyl, heteroalkyl, aryl, aralkyl, heteroaryl, or heteroaralkyl group;
$R^2$ is a substituted or unsubstituted alkyl, heteroalkyl, aryl, aralkyl, heteroaryl, or heteroaralkyl group;
$R^3$ is a substituted or unsubstituted alkyl or heteroalkyl group;
$R^4$ is a substituted or unsubstituted alkyl, heteroalkyl, aryl, aralkyl, heteroaryl, or heteroaralkyl group; and
$R^T$ is hydrogen, PEG, a substituted or unsubstituted alkyl, heteroalkyl aryl, or aralkyl group, or a substituted or unsubstituted alkoxy, aryloxy, or aralkoxy group;
provided that the compound is not A-(C-F-M-F-V) (SEQ ID NO: 1) and is not K-A(C-F-M-F-V) (SEQ ID NO: 2).

In another aspect, the present technology provides composition comprising a compound of Formula I as described herein and a carrier and/or excipient. The composition may be a pharmaceutical formulation that includes an amount of the compound effective for inhibiting *Listeria monocytogenes* virulence, wherein the carrier and/or excipients are pharmaceutically acceptable. The composition may be a disinfectant with an amount of the compound effective for inhibiting *Listeria monocytogenes* biofilm formation on a surface.

In another aspect, the present technology provides methods of modulating QS in *Listeria monocytogenes* comprising contacting *Listeria monocytogenes* with an effective amount of a compound of Formula I as described herein. The compound may activate QS or may inhibit QS.

In another aspect, the present technology provides methods for reducing *Listeria monocytogenes* virulence comprising contacting the *Listeria monocytogenes* with an effective amount of a compound of Formula I as described herein.

In another aspect, the present technology provides methods of inhibiting biofilm formation or growth by *Listeria monocytogenes* on a surface comprising contacting the *Listeria monocytogenes* with an effective amount of a compound of Formula I as described herein. The surface may be a food surface, a food-preparation surface, or a food packaging surface. Hence, there are also provided methods of preventing food-borne listeriosis including applying a composition comprising an effective amount of a compound of Formula I as described herein to a food surface, a food-preparation surface, or a food packaging surface.

In yet another aspect, the present technology provides method of treating a *Listeria monocytogenes* infection in a subject comprising administering to the subject an effective amount of a compound of Formula I as described herein.

BRIEF DESCRIPTION OF THE DRAWINGS

FIG. 1A shows representative activity data of reporter strains with vehicle or with native *L. monocytogenes* AIP over time. FIG. 1B shows selectivity of reporter strains when tested with AIP compounds as discussed in Example 1. All compounds assayed at 10 µM in wild-type reporter (black bars) or ΔagrD reporter (striped bars). Dashed lines signify activity levels of wild-type (top) and ΔagrD (bottom) reporters with vehicle control.

FIG. 5A shows extracted ion chromatograms (EICs) for 699.30+/−0.2 m/z for the wild-type (WT) supernatant (top) and peptide standard mixture (bottom). FIG. 5B shows mass spectra averaged over the peak retention time (RT) for WT and peptide standard mixture.

FIG. 7A shows a portion of the AgrD sequence used to synthesize analogs with demarcations for sequence numbering from C-terminal end. FIG. 7A discloses SEQ ID NO: 32. FIG. 7B shows activation data from screening 10 µM AIP analogs with varying tail lengths in ΔagrD reporter, 10 µM native AIP activation shown for comparison. Data normalized to 1 µM of the native AIP (100%) and media (0%) control.

FIG. 9A is a graph showing AIP and AIP M4dM increase biofilm formation of ΔagrD strain. FIG. 9B is a graph showing KdCdM reduces biofilm of wild-type (WT) strain. FIG. 9C shows the dose-response effect of KdCdM on WT biofilm formation with representative biofilm wells overlaid. Data is normalized to vehicle control of wild-type *L. monocytogenes* (100%) and media control (0%).

DETAILED DESCRIPTION

Figures 1A, 1B:
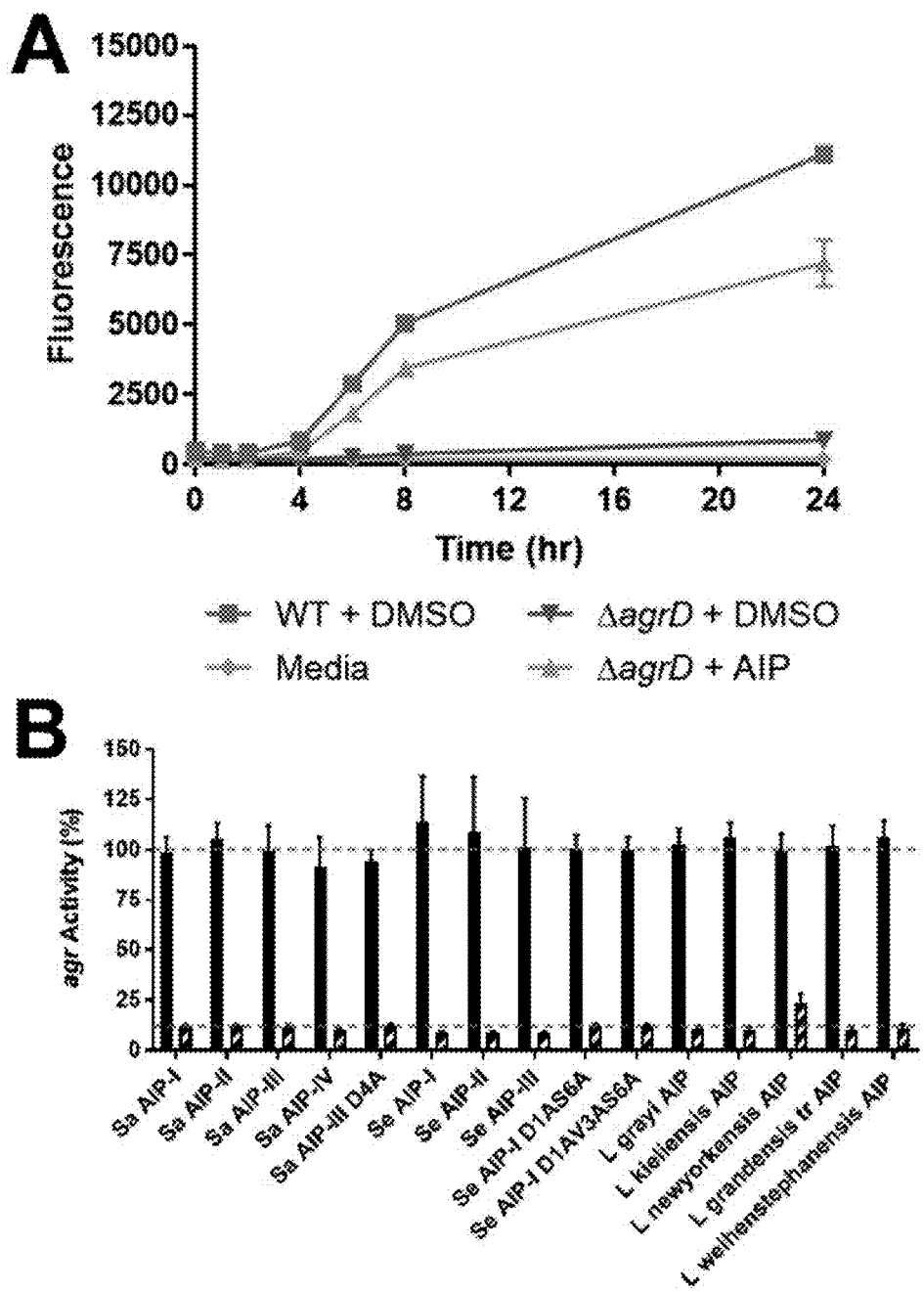
FIGS. 1A and 1B show the validation of the *L. monocytogenes* agr-dependent GFP reporter strain used herein.

The following terms are used throughout as defined below. All other terms and phrases used herein have their ordinary meanings as one of skill in the art would understand.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term that are not clear to persons of ordinary skill in the art, given the context in which it is used, "about" will mean up to plus or minus 10% of the particular term unless otherwise stated or otherwise evident from the context (e.g., where such number would be less than 0% or exceed 100% of a possible value).

"Effective amount" refers to the amount of compound or composition required to produce a desired effect. As the compounds of the present technology may be used in different contexts, the effective amounts may vary with the context in which the compounds are used. For example, the present compounds may be used to reduce virulence of Lm or may be applied to surfaces to inhibit Lm biofilm formation or growth. An effective amount in such contexts may include amounts that inhibit, reduce or eliminate Lm ability to grow or infect, e.g., by slowing, stopping, or reducing Lm growth or biofilm formation on a surface or reproduction on or in a subject. In the context of treatment of a subject, the "effective amount" (i.e., "a therapeutically effective amount") refers to an amount of the compound or composition that alleviates, in whole or in part, symptoms associated with a disorder or disease (e.g., bacterial infection or biofilm formation), or slows or halts further progression or worsening of those symptoms/outcomes. In the context of prevention, an effective amount prevents or provides prophylaxis at least in part for the disease or disorder in a subject at risk for developing the disease or disorder. One example of an effective amount includes amounts or dosages that yield acceptable toxicity and bioavailability levels for therapeutic (pharmaceutical) use. Determining an effective amount of a compound described herein for reducing Lm virulence, inhibiting formation or growth of an Lm biofilm on a surface or treating an Lm infection is well within the skill in the art in view of the present disclosure. Similarly, determining effective amounts of a compound herein for modulating quorum sensing (including activating or inhibiting) is within the skill in the art in view of the guidance provided herein and the general knowledge in the field.

As used herein, a "subject" or "patient" is any animal subject to bacterial infections. In any embodiments, the subject is a human or non-human animal, such as a cat, dog, bird, fish, ungulate, rodent or primate. In any embodiments, the subject is a human. The term "subject" and "patient" can be used interchangeably.

"Treating" or "treatment" within the context of the present technology, means an alleviation, in whole or in part, of symptoms associated with a disorder or disease, or slowing, or halting of further progression or worsening of those symptoms. As a non-limiting example of treatment, a subject can be successfully treated for a bacterial infection (e.g., listeriosis) if, after receiving through administration an effective or therapeutically effective amount of one or more compounds or compositions described herein, the subject shows observable and/or measurable improvements such as reduction or elimination of bacterial load, fever, muscle aches, headache, nausea, vomiting, stiff neck, confusion, loss of balance, convulsions. Treatment, as defined herein, may include administering a compound herein to prevent infection, that is, administering the compound beforehand to avert or forestall the appearance of one or more symptoms of a disease or disorder, such as Lm infection. It will be appreciated by one of skill in the art that prevention is not used as an absolute term. In the medical art it is understood to refer to the prophylactic administration of a drug to substantially diminish the likelihood or seriousness of a condition, or symptom of the condition and this is the sense intended in this disclosure. As used in a standard text in the field, the Physician's Desk Reference, the terms "prevent" "preventing" and "prevention" with regard to a disorder or disease, refer to averting the cause, effects, symptoms or progression of a disease or disorder prior to the disease or disorder fully manifesting itself. Treatment typically refers to the administration of an effective amount of a compound of the present technology to a subject.

Salts, including pharmaceutically acceptable salts, of compounds described herein are within the scope of the present technology and include acid or base addition salts which retain the desired pharmacological activity and are not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydrobromic acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$)ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound in equilibrium with each other, wherein the isomers differ by the position of a hydrogen atom. Common examples of tautomers include keto-enol tautomers and guanidine tautomers. The presence and concentrations of the isomeric forms will depend on the environment the compound is found in and may be different depending upon, for example, whether the compound is a solid or is in an organic or aqueous solution. Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or pharmaceutical compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to a non-hydrogen atom. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include, but are not limited to, alkyl, alkenyl, halogen (i.e., F, Cl, Br, and I); hydroxyl; hydroxyalkyl, alkoxy, alkenoxy, aryloxy, aralkyloxy, heterocyclyl, heterocyclylalkyl, heterocyclyloxy, and heterocyclylalkoxy groups; carbonyl (oxo); carboxylate; ester; urethane; oximes; hydroxylamine; alkoxyamine; aralkoxyamine; thiol; alkylthio; sulfide; sulfoxide; sulfone; sulfonyl; sulfonamide; amine; N-oxide; hydrazine; hydrazide; hydrazone; azide; amide; urea; amidine; guanidine; enamine; imide; isocyanate; isothiocyanate; cyanate; thiocyanate; imine; nitro; nitrile (i.e., CN); and the like.

As to any of the groups herein which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

As used herein, $C_m$-$C_n$, such as $C_1$-$C_{12}$, $C_1$-$C_6$, or $C_1$-$C_3$ when used before a group refers to that group containing m to n carbon atoms.

Alkyl groups include straight chain and branched chain alkyl groups having from 1 to 12 carbon atoms, and typically from 1 to 10 carbons or, in some embodiments, from 1 to 8, 1 to 6, or 1 to 3 carbon atoms. Examples of straight chain alkyl groups include, but are not limited to, groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

Alkoxy groups are hydroxyl groups (—OH) in which the bond to the hydrogen atom is replaced by a bond to a carbon atom of a substituted or unsubstituted alkyl group as defined above. Examples of linear alkoxy groups include, but are not limited to, methoxy, ethoxy, propoxy, butoxy, pentoxy, hexoxy, and the like. Examples of branched alkoxy groups include, but are not limited to, isopropoxy, sec-butoxy, tert-butoxy, isopentoxy, isohexoxy, and the like. Examples of cycloalkoxy groups include, but are not limited to, cyclopropyloxy, cyclobutyloxy, cyclopentyloxy, cyclohexyloxy, and the like. Alkoxy groups may be substituted or unsubstituted. Representative substituted alkoxy groups may be substituted one or more times with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Aryl groups may be substituted or unsubstituted. Representative substituted aryl groups may be mono-substituted or substituted more than once. For example, mono-substituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Aralkyl groups may be substituted or unsubstituted. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanyl-ethyl. Representative substituted aralkyl groups may be substituted one or more times with substituents such as those listed above.

Heteroalkyl groups are $C_{2-12}$ alkyl groups as described above, in which 1, 2, 3, 4, 5, or 6 carbon atoms are replaced with N, O, S, or combinations thereof, in a stable configuration. Thus, the heteroalkyl groups may include for example, NH, O, S, S(O) and $SO_2$ groups. Heteroalkyl groups have at least one carbon and do not include groups bearing adjacent heteroatoms (e.g., peroxides). In any embodiments, heteroalkyl groups include one or two heteroatoms selected from NH, O and S, wherein each heteroatom may be the same or different. Where valence allows, heteroalkyl groups may be further substituted with substituents as described herein. Examples of heteroalkyl groups include, but are not limited —$CH_2CH_2SCH_3$, —$CH_2CH_2OCH_2CH_3$, —$CH_2CH_2N(CH_3)CH_2SCH_3$, —$OCH_2CH_2OCH_2CH_2OCH_3$, —$CH_2S(O)CH_2$, —$CH_2CH_2SO_2CH_3$, and the like, as well as, e.g., polyether and polyamino alkyl groups, including but not limited to poly(oxyalkylene) groups.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Heterocyclyl groups may be substituted or unsubstituted. Representative substituted heterocyclyl groups may be monosubstituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. The phrase "heteroaryl groups" includes fused ring compounds. Heteroaryl groups may be substituted or unsubstituted. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, for example, chloroethyl is not referred to herein as chloroethylene.

The terms "alkanoyl" and "alkanoyloxy" as used herein can refer, respectively, to —C(O)— alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Aryloxy and arylalkoxy groups may each be may be substituted or unsubstituted. Representative substituted aryloxy and arylalkoxy groups may be substituted one or more times with substituents such as those listed above.

The term "carboxyl" as used herein refers to a —COOH group or its ionized form, —COO$^-$.

The term "ester" as used herein refers to —COOR$^{70}$ and —C(O)O-G groups. R$^{70}$ is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) (also referred to as carboxamide) and formamide groups (—NHC(O)H). In some embodiments, the amide is —NR$^{71}$C(O)—(C$_{1-5}$ alkyl)

and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino (i.e., —NHalkyl), dialkylamino (i.e., —N(alkyl)$_2$), arylamino (i.e., —NHaryl), or alkylarylamino (i.e., —N(alkyl)(aryl)). In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while "sulfides" include —SR$^{80}$ groups, "sulfoxides" include —S(O)R$^{81}$ groups, "sulfones" include —SO$_2$R$^{82}$ groups, and "sulfonyls" include —SO$_2$OR$^{83}$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{84}$—C(O)—NR$^{85}$R$^{89}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and —NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{94}$)=C(R$^{95}$)NR$^{96}$R$^{97}$ and —NR$^{94}$C(R$^{95}$)=C(R$^{96}$)R$^{97}$, wherein R$^{94}$, R$^{95}$, R$^{96}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O$^-$. A "hydroxyalkyl" group is a hydroxyl-substituted alkyl group, such as HO—CH$_2$—.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{100}$(NR$^{101}$) and —N(CR$^{100}$R$^{101}$) groups, wherein R$^{100}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkyl ammonium" refers to a —N(alkyl)$_3$ group. A trialkylammonium group is positively charged and thus typically has an associated anion, such as halogen anion.

The term "isocyano" refers to —NC.

The term "isothiocyano" refers to —NCS.

The term "amino acid" refers to any natural or unnaturally occurring alpha-amino acids. Stereochemistry at the alpha carbon may be L, D, or a mixture there of Except where indicated as encompassing both D and/or L or where expressly defined as D, proteinogenic amino acids have L stereochemistry at the alpha carbon.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

The present technology provides compounds that may be used to modulate quorum sensing by Lm. In one aspect, the present technology provides compounds of Formula I

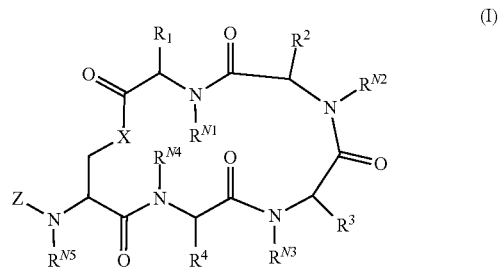

(I)

stereoisomers thereof, and/or salts thereof, wherein
X is S, O, NH, NR, $CH_2$ or CH, provide that the CH forms a double bond with the adjacent carbon;
Z is $R^T$, $R^T$—C(O), an amino acid residue, or a peptide of 2-10 amino acid residues, wherein Z is optionally attached to a solid substrate;
R is an unsubstituted $C_{1-6}$ alkyl group;
$R^{N1}$, $R^{N2}$, $R^{N3}$, $R^{N4}$, and $R^{N5}$ are each independently H or $CH_3$;
$R^1$ is a substituted or unsubstituted alkyl, heteroalkyl, aryl, aralkyl, heteroaryl, or heteroaralkyl group;
$R^2$ is a substituted or unsubstituted alkyl, heteroalkyl, aryl, aralkyl, heteroaryl, or heteroaralkyl group;
$R^3$ is a substituted or unsubstituted alkyl or heteroalkyl group;
$R^4$ is a substituted or unsubstituted alkyl, heteroalkyl, aryl, aralkyl, heteroaryl, or heteroaralkyl group; and
$R^T$ is hydrogen, PEG, a substituted or unsubstituted alkyl, heteroalkyl, aryl, or aralkyl group, or a substituted or unsubstituted alkoxy, aryloxy, or aralkoxy group;
provided that the compound is not A-(C-F-M-F-V) (SEQ ID NO: 1) and is not K-A(C-F-M-F-V) (SEQ ID NO: 2).

In any embodiments of the compounds of Formula (I),
$R^1$ is an unsubstituted $C_{1-6}$ alkyl group, or a substituted or unsubstituted phenyl or a benzyl group;
$R^2$ and $R^4$ are independently selected from an unsubstituted $C_{1-6}$ alkyl group, or a substituted or unsubstituted phenyl, benzyl, indolyl, or indolylmethyl group;
$R^3$ is an unsubstituted $C_{1-6}$ alkyl group, a $C_{1-6}$ alkylene-thioalkyl group, a $C_{1-6}$ alkylene-oxyalkyl group, or a $C_{1-6}$ hydroxyalkyl group;
$R^T$ is hydrogen or a substituted or unsubstituted $C_{1-6}$ alkyl group; or, when Z is $R^T$—C(O), $R^T$ is —$OR^5$, wherein $R^5$ is a substituted or unsubstituted $C_{1-6}$ alkyl, benzyl or fluorenylmethyl group; and
each substituent present on any substituted group is independently selected from halogen, hydroxyl, unsubstituted $C_{1-6}$ alkyl, amino-substituted $C_{1-6}$ alkyl, $C_{1-6}$ alkoxy, amino, $C_{1-6}$ alkylamino, di-$C_{1-6}$-alkyl amino, $C_{1-6}$ haloalkyl, $C_{1-6}$ haloalkoxy, thiol, $C_{1-6}$ alkylthio, —$CO_2R^a$ where $R^a$ is hydrogen or an unsubstituted $C_{1-6}$ alkyl, —COR', where R' is H or an unsubstituted $C_{1-6}$ alkyl group, —CO—$NR''_2$, where each R" is independently hydrogen or $C_{1-6}$ alkyl, azido, nitro, cyano, isocyano, thiocyano, isothiocyano, cyanate, isocyanate, thiocyanate, or isothiocyanate groups;
provided that the compound is not A-(C-F-M-F-V) (SEQ ID NO: 1) and is not K-A(C-F-M-F-V) (SEQ ID NO: 2).

In any embodiments of compounds of Formula (I), X may be S. In any embodiments, X may be O. In any embodiments, X may be NH. In any embodiments, X may be NR such as $NCH_3$. In any embodiments X is CH2. In any embodiments, X is CH, provide that the CH forms a double bond with the adjacent carbon.

In any embodiments of the compounds of Formula (I), Z may be a variety of moieties. For example, Z may be an amino acid residue or a peptide of 2-10 (i.e., 2, 3, 4, 5, 6, 7, 8, 9, or 10) amino acid residues. The amino acids may be naturally occurring or unnatural (e.g., synthetic) amino acids. In any embodiments, Z may be an amino acid residue or a dipeptide. For example Z may be an amino acid residue selected from any of the 20 naturally occurring amino acids found in proteins or their enantiomers. Non-limiting examples include alanine, lysine, serine, methionine, aspartic acid, proline, and valine residues. In any embodiments, Z may be selected from an alanine, valine, or lysine residue, or a lysine-alanine dipeptide. In any embodiments, the amino acid residue or peptide of Z may be optionally N-methylated. In any embodiments, Z may be $R^T$ or $R^T$—C(O). In some embodiments, $R^T$ is hydrogen or a methyl group. In others, $R^T$ may be OR. In some such embodiments, R may be methyl, ethyl, propyl, t-butyl, benzyl, or fluorenylmethyl.

As noted herein, in compounds of Formula (I), $R^{N1}$, $R^{N2}$, $R^{N3}$, $R^{N4}$, and $R^{N5}$ are each independently H or a methyl group. In any embodiments each of $R^{N1}$, $R^{N2}$, $R^{N3}$, $R^{N4}$, and $R^{N5}$ may each be H. In any embodiments, one of $R^{N1}$, $R^{N2}$, $R^{N3}$, $R^{N4}$, and $R^{N5}$ may be a methyl group and the rest may be H.

As defined herein, $R^1$ may be a variety of moieties, including a substituted or unsubstituted alkyl, heteroalkyl, aryl, aralkyl, heteroaryl, or heteroaralkyl group. In any embodiments, $R^1$ may be a substituted or unsubstituted $C_{1-6}$ alkyl group. For example, $R^1$ may a substituted or unsubstituted $C_{3-6}$ branched alkyl group. Non-limiting examples of such include isopropyl, sec-butyl, and isobutyl.

As defined herein, $R^2$ may be a substituted or unsubstituted alkyl, heteroalkyl, aryl, aralkyl, heteroaryl, or heteroaralkyl group. In any embodiments, $R^2$ may be a substituted or unsubstituted $C_{3-6}$ alkyl group, or an aralkyl or heteroaralkyl group. For example, $R^2$ may be benzyl, para-hydroxy benzyl, imidazolylmethyl, or indolylmethyl. In any embodiments, $R^2$ may be substituted or unsubstituted benzyl. In some such embodiments, the benzyl is unsubstituted or substituted with one or more (e.g., 1, 2, or 3) of hydroxyl, halogen, carboxyl, amino, amine, nitro, alkoxy, $C_{1-6}$ alkyl, $C_{1-6}$ halo alkyl, or $C_{1-6}$ hydroxy alkyl groups.

As defined herein, $R^3$ may be a substituted or unsubstituted alkyl or heteroalkyl group. In any embodiments, $R^3$ may be an unsubstituted $C_{1-6}$ alkyl or $C_{2-6}$ heteroalkyl group. For example, $R^3$ may be a methyl, ethyl, or ethylene-S-methyl group.

As defined herein, $R^4$ may be a substituted or unsubstituted alkyl, heteroalkyl, aryl, aralkyl, heteroaryl, or heteroaralkyl group. In any embodiments, $R^4$ may be a substituted or unsubstituted $C_{3-6}$ alkyl group, or an aralkyl or heteroaralkyl group. For example, $R^4$ may be a benzyl, para-hydroxy benzyl, imidazolylmethyl, or indolylmethyl group. In any embodiments, $R^4$ may be substituted or unsubstituted benzyl. In some such embodiments, the benzyl is unsubstituted or substituted with one or more (e.g., 1, 2, or 3) of hydroxyl, halogen, carboxyl, amino, amine, nitro, alkoxy, $C_{1-6}$ alkyl, $C_{1-6}$ halo alkyl, or $C_{1-6}$ hydroxy alkyl groups Compounds of Formula (I) include stereoisomers. In any embodiments, the stereochemistry of all amino acid residues is L and may have, e.g., the structure of Formula IA:

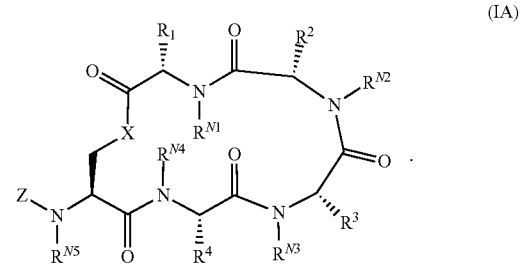

(IA)

In any embodiments of the compounds of Formula I, the stereochemistry of one or more amino acid residues is D. In any embodiments, the stereochemistry of the amino acid residue at position 5 of Formula I is D (numbering of positions is shown below).

$$\text{(I)}$$

In any embodiments of compounds of Formula I, the stereochemistry of the amino acid residue at position 3 of Formula I is D. In any embodiments, the stereochemistry of the amino acid residues at position 5 is D. In any embodiments, the stereochemistry at positions 3 and 5 is D.

In any embodiments of compounds of Formula I (including IA), each substituent present may be independently selected from halogen, hydroxyl, unsubstituted $C_{1-6}$ alkyl, amino-substituted $C_{1-6}$ alkyl, $C_{1-6}$ alkoxy, amino, $C_{1-6}$ alkylamino, di-$C_{1-6}$-alkyl amino, $C_{1-6}$ haloalkyl, $C_{1-6}$ haloalkoxy, thiol, $C_{1-6}$ alkylthio, —$CO_2R^a$ where $R^a$ is hydrogen or an unsubstituted $C_{1-6}$ alkyl, —COR', where R' is H or an unsubstituted $C_{1-6}$ alkyl group, —CO—NR''$_2$, where each R'' is independently hydrogen or unsubstituted $C_{1-6}$ alkyl, azido, nitro, cyano, isocyano, thiocyano, isothiocyano, cyanate, isocyanate, thiocyanate, or isothiocyanate groups. In any embodiments, each substituent present may be independently selected from halogen, hydroxyl, amino, guanidine, carboxyl, carboxamide, and thiol. In any embodiments, a substituted group may have one or two substituents.

In any embodiments, the compound may be selected from the group consisting of A-(C-F-dM-F-V), V-(C-F-M-F-V) (SEQ ID NO: 3), K-A-(dC-F-dM-F-V), and K-(dC-F-dM-F-V).

The present technology provides compositions including any of the compounds disclosed herein and a carrier and/or excipient. Thus in any embodiments, the compositions are pharmaceutical compositions and medicaments comprising any one of the embodiments of the compounds disclosed herein and one or more pharmaceutically acceptable carriers and/or excipients. The compositions may be used in the methods and treatments described herein. Thus, in any embodiments, the compositions may include an amount of the compound effective for inhibiting *Listeria monocytogenes* virulence, wherein the carrier and/or excipients are pharmaceutically acceptable, and the composition is a pharmaceutical composition. In any embodiments, the pharmaceutical composition may include an effective amount of any of one of the embodiments of the compounds or compositions disclosed herein for modulating quorum sensing in bacteria, e.g., Gram-positive bacteria such as *Listeria monocytogenes*. In any embodiments, the effective amount may be an effective amount for activating quorum sensing by *Listeria monocytogenes* or inhibiting quorum sensing by *Listeria monocytogenes*. In any embodiments of the compositions, including embodiments of pharmaceutical compositions, the effective amount may be effective for inhibiting biofilm formation and/or growth by *Listeria monocytogenes*. In any embodiments, the amount of the compound in the composition is effective for inhibiting *Listeria monocytogenes* biofilm formation on a surface and the composition is a disinfectant. In any embodiments of the compositions, the compound may be selected from one in which the stereochemistry of the amino acid residue at position 3 or position 3 and 5 of Formula (I) is D. In any embodiments of the compositions, the compound may be selected from K-A-(dC-F-dM-F-V), and K-(dC-F-dM-F-V).

The compositions described herein can be formulated for use on surfaces (e.g., as disinfectants), including as aqueous solutions or suspensions, non-aqueous solutions or suspensions, or creams, pastes, gels or the like. Thus, the compositions may be sprayed, cast or rubbed on a surface, or applied with a cloth, sponge, roller, or any suitable applicator known in the art. The compositions may formulated as a coating with suitable polymers and other agents to provide long lasting antibacterial (i.e., anti Lm) activity over days (e.g., 1, 2, 3, 4, 5, or 6), weeks (e.g., 1, 2, or 3), months (e.g., 1-11) or even up to a year after application to a surface. The effective amount of a compound described herein may be from 0.0001 wt % to 10 wt % based on the total weight of the composition, depending on the intended use and delivery route. In any embodiments, the effective amount may be 0.0001 wt %, 0.0005 wt %, 0.001 wt %, 0.005 wt %, 0.01 wt %, 0.05 wt %, 0.1 wt %, 0.5 wt %, 1 wt %, 2 wt %, 5 wt %, 10 wt % or a range between or including any two of the foregoing values. For example, in any embodiments, the effective amount may be from 0.01 wt % to 1 wt %.

The compositions described herein can also be formulated for various routes of administration to treat or prevent infection, for example, by oral, parenteral, topical, injection, rectal, nasal, vaginal administration, or via implanted reservoir (or may simply be part of a coating on the surface of the implant in contact with tissue). Parenteral or systemic administration includes, but is not limited to, subcutaneous, intravenous, intraperitoneal, and intramuscular injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds disclosed herein, or pharmaceutically acceptable salts or stereoisomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include solutions or aqueous suspensions which may be prepared using a suitable dispersant or wetting agent and a suspending agent so long as such agents do not interfere with the activity of the drugs described herein. Injectable forms may be prepared with acceptable solvents or vehicles including, but not limited to sterilized water, Ringer's solution, 5% dextrose, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology also may be formulated as a composition for topical administration (e.g., creams, ointments, gels, foams, transdermal patch, wound dressing, and the like). These formulations may contain various excipients known to those skilled in the art. Suitable excipients may include, but are not limited to, cetyl esters wax, cetyl alcohol, white wax, glyceryl monostearate, propylene glycol monostearate, methyl stearate, benzyl alcohol, sodium lauryl sulfate, glycerin, mineral oil, water, carbomer, ethyl alcohol, acrylate adhesives, polyisobutylene adhesives, and silicone adhesives.

Dosage units for rectal administration may be prepared in the form of suppositories which may contain the composition of matter in a mixture with a neutral fat base, or they may be prepared in the form of gelatin-rectal capsules which contain the active substance in a mixture with a vegetable oil or paraffin oil.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. Formulations for inhalation administration contain as excipients, for example, lactose, polyoxyethylene-9-lauryl ether, glycocholate and deoxycholate. Aqueous and nonaqueous aerosols are typically used for delivery of inventive compounds by inhalation.

Ordinarily, an aqueous aerosol is made by formulating an aqueous solution or suspension of the compound together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions. A nonaqueous suspension (e.g., in a fluorocarbon propellant) can also be used to deliver compounds of the present technology.

Aerosols containing compounds for use according to the present technology are conveniently delivered using an inhaler, atomizer, pressurized pack or a nebulizer and a suitable propellant, e.g., without limitation, pressurized dichlorodifluoromethane, trichlorofluoromethane, dichlorotetrafluoroethane, nitrogen, air, or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch. Delivery of aerosols of the present technology using sonic nebulizers is advantageous because nebulizers minimize exposure of the agent to shear, which can result in degradation of the compound.

For nasal administration, the pharmaceutical formulations and medicaments may be a spray, nasal drops or aerosol containing an appropriate solvent(s) and optionally other compounds such as, but not limited to, stabilizers, antimicrobial agents, antioxidants, pH modifiers, surfactants, bioavailability modifiers and combinations of these. For administration in the form of nasal drops, the compounds may be formulated in oily solutions or as a gel. For administration of nasal aerosol, any suitable propellant may be used including compressed air, nitrogen, carbon dioxide, or a hydrocarbon based low boiling solvent.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference. Thus, the present technology provides a pharmaceutical composition comprising any polymer-drug conjugate as described herein and a pharmaceutically acceptable carrier or excipient.

Specific dosages for therapy may be adjusted depending on conditions of disease, the age, body weight, general health conditions, sex, and diet of the subject, dose intervals, administration routes, excretion rate, and combinations of compounds. Any of the above dosage forms containing effective amounts are well within the bounds of routine experimentation and therefore, well within the scope of the instant present technology.

A therapeutically effective amount of a compound of the present technology may vary depending upon the route of administration and dosage form. Effective amounts of such compounds typically fall in the range of about 0.01 up to about 100 mg/kg/day, or about 0.05 to about 50 mg/kg/day, and may fall in the range of about 0.1 up to 5 mg/kg/day. Typically, the compound or compounds of the instant technology are selected to provide a formulation that exhibits a high therapeutic index. The therapeutic index is the dose ratio between toxic and therapeutic effects and can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Effective amounts of compounds of the present technology may be administered by various routes as described herein and may be given all at once or take place over a period of time including but not limited to 5 minutes, 10 minutes, 20 minutes, 30 minutes, 45 minutes, 1 hour, 2 hours, 3 hours, 5 hours, 10 hours, 12, hours, 15 hours, 20 hours, 24 hours or a range between and including any of the foregoing values. The frequency of administration may vary, for example, once or twice per day, per 2 days, per 3 days, per week, per 10 days, per 2 weeks, every other day, or a range between and including any of the foregoing frequencies. Alternatively, the compositions may be administered once per day on 2, 3, 4, 5, 6 or 7 consecutive days. A complete regimen may thus be completed in only a few days or over the course of 1, 2, 3, 4, 5, 6 or more weeks.

In another aspect, the present technology provides methods for modulating quorum sensing in *Listeria monocytogenes*. The methods include contacting *Listeria monocytogenes* with an effective amount of any compound disclosed herein, including but not limited to a compound of Formula I or IA. In any embodiments of the methods, the compound may be selected from A-(C-F-dM-F-V), V-(C-F-M-F-V) (SEQ ID NO: 3), and quorum sensing by *Listeria monocytogenes* is activated. In any embodiments, the compound may be selected from K-A-(dC-F-dM-F-V), and K-(dC-F-dM-F-V), and quorum sensing by *Listeria monocytogenes* is inhibited. It will be appreciated that compounds of the present technology that inhibit quorum sensing may also be effective in one or more of reducing Lm virulence, inhibiting biofilm formation, and/or treating Lm infections.

In another aspect, the present technology provides methods for reducing *Listeria monocytogenes* virulence. The methods include contacting the *Listeria monocytogenes* with an effective amount of any compound disclosed herein. In any embodiments, the compound may be selected from one in which the stereochemistry of the amino acid residue at position 3 or position 3 and 5 of Formula (I) is D. In any embodiments, the compound may be selected from K-A-(dC-F-dM-F-V) and/or K-(dC-F-dM-F-V).

In another aspect, the present technology provides methods of inhibiting biofilm formation by *Listeria monocytogenes* on a surface comprising contacting *Listeria monocytogenes* with an effective amount of a compound disclosed herein. In any embodiments, the compound may be selected from one in which the stereochemistry of the amino acid residue at position 3 or position 3 and 5 of Formula (I) is D. In any embodiments, the compound may be selected from K-A-(dC-F-dM-F-V) and K-(dC-F-dM-F-V). In any embodiments, the methods further include applying the effective amount of the compound to the surface. The surface includes any one on which Lm may grow and form biofilms. In any embodiments, the surface may be a food surface, a food storage or preparation surface, or a food packaging surface. For example, the food surface may be the surface of a fruit or vegetable, an animal carcass, meat, poultry, or fish, or even sauces and condiments. Food may also include animal food, such as silage. Food storage and preparation surfaces may include but are not limited to counter tops, shelves, cupboards, racks, refrigerators, stove tops, ovens, bowls, utensils, cups, plates, boards, tables, and the surfaces of other food processing equipment (e.g., mixers, blenders, vats, shredders, grinders, valves, piping, pumps, screens, slicers, separators, forming equipment, and the like). Hence, there are also provided methods of preventing food-borne listeriosis including applying a composition comprising an effective amount of a compound as described herein to a food surface, a food-preparation surface, or a food packaging surface.

In another aspect, the present technology provides methods of treating a *Listeria monocytogenes* infection in a subject comprising administering an effective amount of any of the compounds disclosed herein. The subject may be a human or a non-human animal. Thus the subject may be selected from a variety of non-human animals such as domestic pets (cats, dogs, gerbils, hamsters, hedgehogs, birds, and the like), livestock such as poultry, ruminants, and the like. In any embodiments, the subject may be selected from the group consisting of cattle, sheep, buffalo and goats. In any embodiments, the compound may be selected from one in which the stereochemistry of the amino acid residue at position 3 or position 3 and 5 of Formula (I) is D. In any embodiments, the compound may be selected from K-A-(dC-F-dM-F-V) and K-(dC-F-dM-F-V). The compound may be administered by any route disclosed herein, including systemically, or to treat skin infections, topically. In any embodiments, the methods further include administering an effective amount of a second therapeutic agent such as a different class of antibiotics. Thus the compound of the present technology may be administered with an effective amount of the second therapeutic agent separately, sequentially, or simultaneously.

The examples herein are provided to illustrate advantages of the present technology and to further assist a person of ordinary skill in the art with preparing or using the drugs of the present technology. To the extent that the compositions include ionizable components, salts such as pharmaceutically acceptable salts of such components may also be used. The examples herein are also presented in order to more fully illustrate certain aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

Materials and General Methods

Reagents and strains. All standard reagents were purchased from commercial sources and used according to sources' instructions. Strains, plasmids, and primers are summarized in Tables 1-2. For standard methods, *L. monocytogenes* strains EGD-e and ΔagrD were cultured in brain heart infusion (BHI, from Teknova), while the corresponding fluorescent EGD-e and ΔagrD strains were grown in BHI supplemented with 10 μg/mL chloramphenicol. For biofilm assays, *L. monocytogenes* EGD-e and ΔagrD biofilms were grown in Lysogeny Broth (LB, from Research Products International). Overnight cultures were grown in 3 mL of media (with antibiotic if appropriate) at 37° C. with 200 rpm shaking unless noted otherwise. C. Riedel provided EGD-e and ΔagrD strains.

TABLE 1

Bacterial strains and plasmids used in the Examples

| Strain/plasmid | Characteristics | Reference/source |
|---|---|---|
| Strains | | |
| L. monocytogenes EGD-e | Wild-type L. monocytogenes lab strain | |
| L. monocytogenes EGD-e ΔagrD | In-frame deletion of agrD in EGD-e background | Riedel et al., 2009 |
| L. monocytogenes EGD-e: pAM401-KW1 | EGD-e with plasmid for agr-dependent GFP expression | Present Examples |
| L. monocytogenes EGD-e ΔagrD: pAM401-KW1 | EGD-e ΔagrD with plasmid for agr-dependent GFP expression | Present Examples |
| E. coli XL1-Blue | Cloning host strain | Agilent |
| E. coli S17 | Plasmid conjugation strain | Simon et al., 1983 |
| Plasmids | | |
| pAM401 | E. coli-Listeria shuttle vector, Cm$^r$ | Wirth et al., 1986 |
| pAM401-KW1 | Super folder gfp under control of L. monocytogenes agr promoter inserted into pAM401 | Present Examples |

TABLE 2

Primers used in this study.

| Primer | Sequence | Characteristics | Reference/source |
|---|---|---|---|
| DAP337 | AAT CCA TGC CAA CCC GTT CCA TGT (SEQ ID NO: 4) | Forward primer to verify pAM401 insert | Present Examples |
| DAP338 | ACG CAT CGT GGC CGG CAT C (SEQ ID NO: 5) | Reverse primer to verify pAM401 insert | Present Examples |

Construction of *Listeria* agr Reporter Strains. A gene block was designed and purchased from Integrated DNA Technologies to contain an EagI recognition site, the $P_{II}$ promoter of the agr system, the 3' UTR of hly, super folder GFP, and a SalI recognition site. The gene block was digested with EagI and SalI, cloned into an EagI/SalI-cut pAM401 plasmid resulting in the plasmid pAM401-KW1, and then transformed into *E. coli* XL1-Blue competent cells. The insertion into pAM401 was confirmed using Kapa polymerase and primers DAP337 and DAP338, and additional confirmation via commercial sequencing. Purified plasmid was transformed into the conjugative *E. coli* S17 strain, which was used to conjugate to EGD-e and EGD-e ΔagrD to generate the agr-GFP reporter strains EGD-e: pAM401-KW1 and EGD-e ΔagrD:pAM401-KW1. Conjugation was verified using primers DAP337 and DAP338.

Fluorescence reporter assay protocol. For QS (agr) reporter assays, peptide stock solutions in DMSO (1 mM) were serially diluted in DMSO, and 2 μL of solution was added to each well in a black 96-well plate (polystyrene microtiter plate, Costar). Agonism assays utilized the ΔagrD reporter strain, with 2 μL of 100 μM AIP (final concentration 1 μM) as a positive control and 2 μL of DMSO as a negative control. Antagonism assays utilized the EGD-e reporter strain, with 2 μL of DMSO as a positive control. In both assays, wells containing only BHI media served as negative controls for normalization. An overnight culture of bacteria was diluted 1:50 in fresh BHI, then 198 μL were transferred to each well (excluding the media control wells). Plates were then incubated at 37° C. for 24 hours with shaking at 200 rpm. Fluorescence of GFP (excitation at 500 nm, emission at 540 nm) and $OD_{600}$ of each well was measured using BioTek Synergy 2 plate reader. Measurements were processed by subtracting background fluorescence (BHI media), correcting by $OD_{600}$, and the normalizing using the 1 μM AIP or the DMSO control for the agonism and antagonism assays, respectively. Non-linear regression curves were fitted to the data sets in GraphPad Prism 7 by using variable slope (four-parameter) dose-response analysis to obtain potency, efficacy, and statistical information about the activity of tested peptides. Each peptide was tested with three technical replicates and three biological replicates. All data derived from fluorescent reporter strains are represented with data points signifying the mean and error bars signifying the standard deviation from all replicates.

Biofilm assay protocol. Biofilms assays were adapted from previous reports and protocols.[51-52] Overnight cultures of *L. monocytogenes* EGD-e and ΔagrD were grown in BHI, then diluted 1:100 in LB. For single-point assays, 2 μL of agonists or antagonists at an appropriate concentration were added to wells in a clear 96-well microtiter plates. For dose-response assays, a stock solution of the select peptide were serially diluted in DMSO, then 2 μL of each concentration were transferred to the appropriate wells. Then, 198 μL of bacteria were added to their respective wells, using ΔagrD for agonist wells and EGD-e for antagonist wells. In each plate, additional vehicle controls for baseline biofilm formation of EGD-e and ΔagrD strains (2 μL of DMSO) were included, as well as a media control (200 μL of LB). Plates were incubated at room temperature for 24 hours statically, at which point plates were inverted over a glass waste container and gently shook to remove planktonic bacteria. The wells were gently washed with 200 μL of PBS twice, inverting again over the waste container to remove liquid. Then, 200 μL of 0.1% crystal violet solution (in water) were added to each well and incubated for 30 minutes. The wells were then washed with 200 μL of PBS three more times and left to air dry for 15 minutes. Remaining crystal violet was solubilized by the addition of 100 μL of 95% ethanol in water solution, pipetting up and down to mix, incubated for 10 minutes, then absorbance was read at 595 nm. Absorbance data was processed by normalizing to the EGD-e vehicle control (100%) and the LB media control (0%). Non-linear regression curves were fitted to the data sets in GraphPad Prism 7 by using variable slope (four-parameter) dose-response analysis to obtain potency, efficacy, and statistical information about the activity of tested peptides. Each well was tested with four technical replicates and three biological replicates. All data derived from crystal violet biofilm assays are represented with data points signifying the mean and error bars signifying the standard deviation from all replicates.

Example 1

Preparation and Validation of *Listeria* agr Reporter Strains. In order to facilitate profiling the native AIP and its analogs for agr activity, *L. monocytogenes* agr GFP reporters were designed and constructed as described above (see Materials and General Methods). Briefly, a plasmid containing the agr promoter region upstream of gfp was transformed into wild-type (EGD-e) and ΔagrD *L. monocytogenes* strains. The wild-type reporter naturally produces its own AIP and is able to activate AgrC, which may subsequently phosphorylate AgrA for productive binding to DNA and triggering the production of GFP (FIG. 1A). The ΔagrD reporter, lacking the ability to produce its own AIP and thereby activate AgrC, is unable to trigger substantial production of GFP. However, adding exogenous AIP to the ΔagrD reporter results in an increase of fluorescence, indicating agr activity has been restored. As expected, these results suggest that the production of GFP in these reporter strains is dependent on activation of the agr system via AIP binding.

The activity seen in these reporter strains was also highly specific for the *L. monocytogenes* AIP, as AIPs from other species (see Examples 2 and 3 below) showed little or no activity at all in either of the reporter strains (FIG. 1B). This result was unexpected as non-cognate AIPs often antagonize AgrC receptors.[36-39]

Example 2

Figure 2:
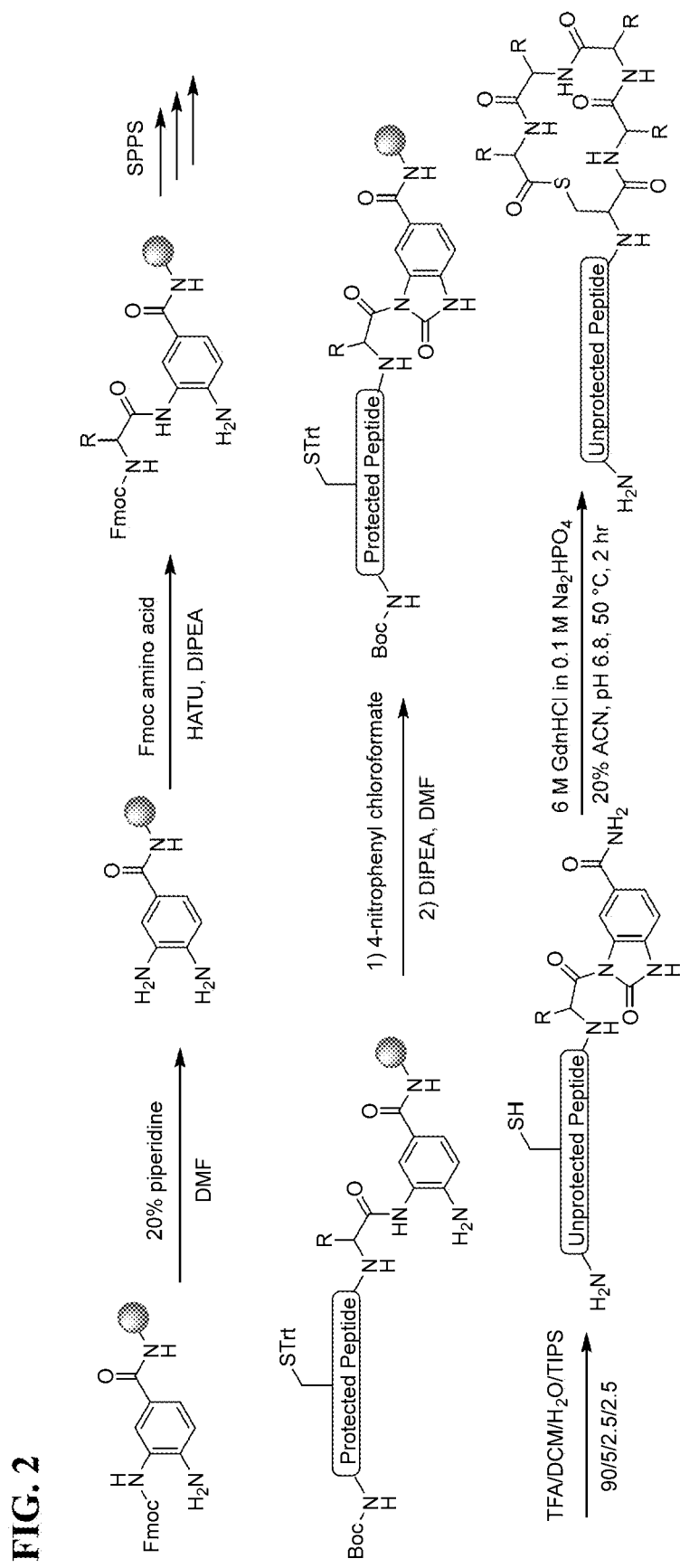
FIG. 2 shows a solid-phase synthetic scheme for illustrative compounds of the present technology where X═S.
Figure 3:
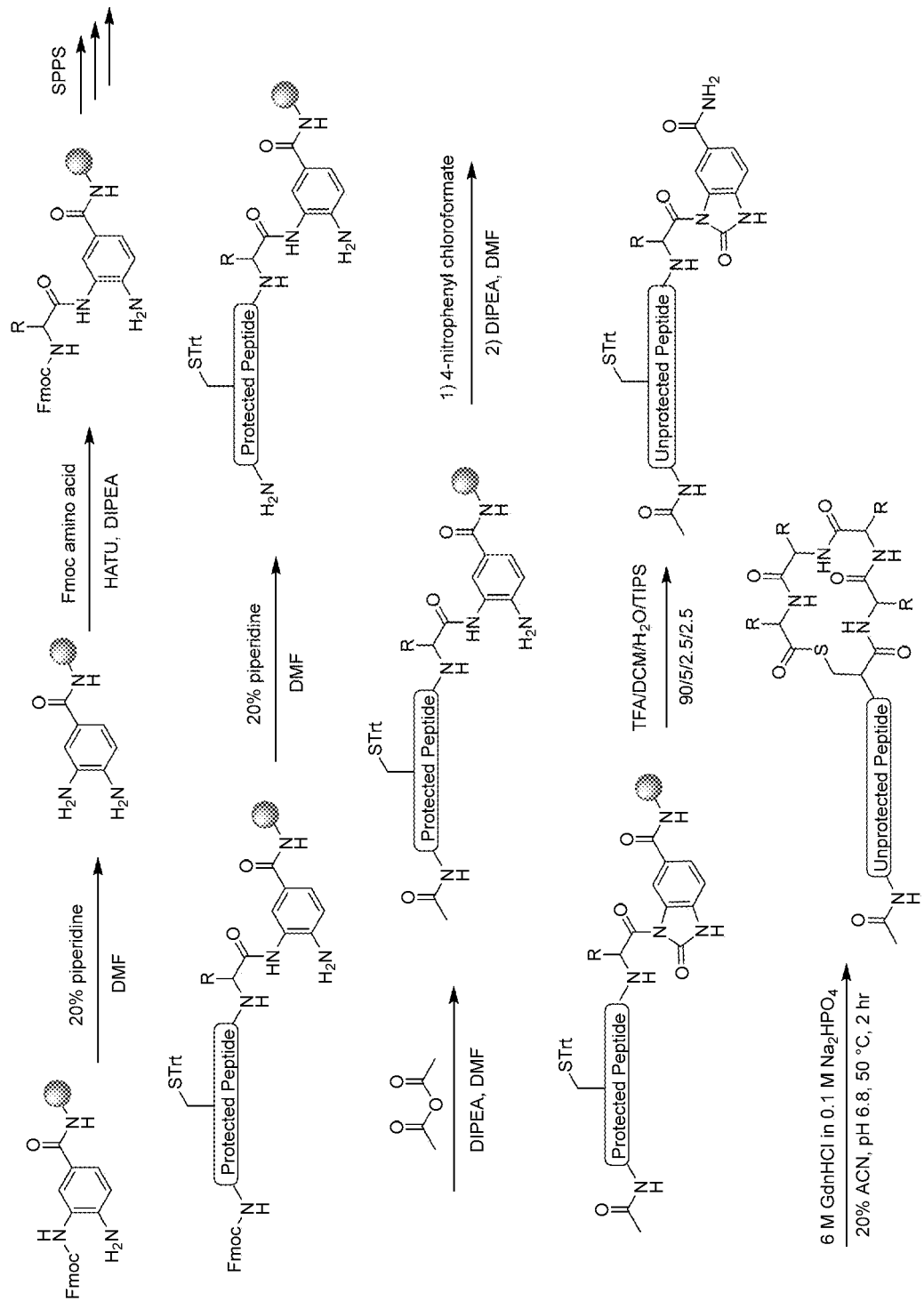
FIG. 3 shows a solid-phase synthetic scheme for N-acyl (e.g., acetylated) compounds of the present technology.
Figure 4:
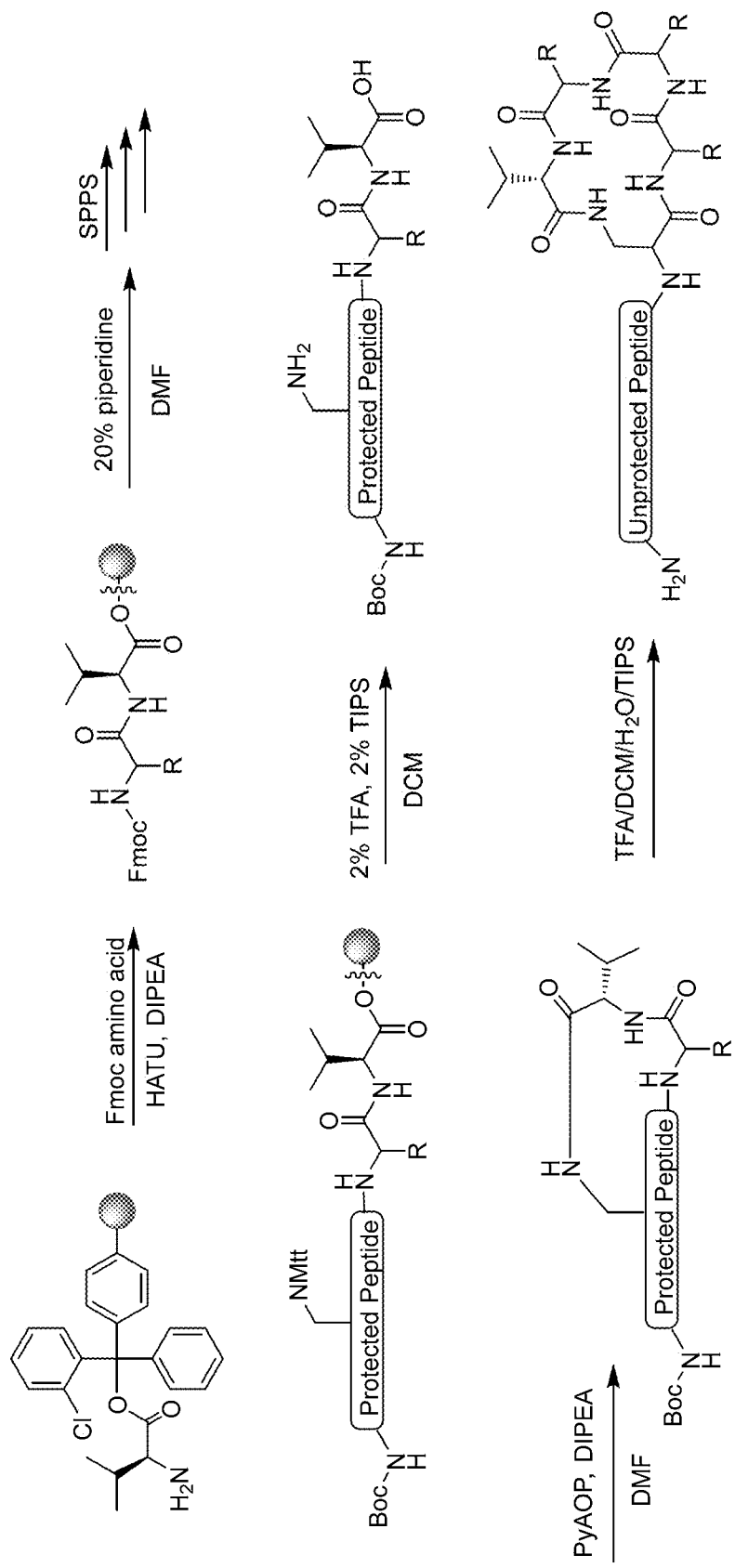
FIG. 4 shows a solid-phase synthetic scheme for illustrative compounds of the present technology where X is NH.

Peptide synthesis. Compounds of the present technology (also referred to herein as AIP analogs) were synthesized on solid-phase resin, purified using reverse-phase high-performance liquid chromatography (HPLC), and characterized using high-resolution mass spectrometry (HRMS) and analytical HPLC, following previously characterized methods.[45, 50] FIGS. 2-4 summarize the relevant synthetic schemes used. Table 3 below summarizes the compounds prepared and provides relevant high resolution mass spectroscopy data calculated and observed [M+H]$^+$, and HPLC data (retention time and purity).

Standard thioester AIP analog peptide synthesis. Thioester AIP peptides were synthesized accordingly to previous protocols (shown in FIG. 2).[53-54] Approximately 30 mg (0.0147 mmol, 1 eq.) of Fmoc Dawson Dbz AM resin was swelled in a vessel of DCM for at least 40 min, then subsequently washed with DCM (2 mL×3) and DMF (2 mL×3). The washed resin was then deprotected with 20% piperidine in DMF (2 mL×3 for 5, 5, and 10 minutes) while shaking the vessel. After washing the resin with DMF (2 mL×3), the first amino acid for loading was prepared. The appropriate N$^\alpha$-Fmoc protected amino acid (4 eq.), HATU (4 eq.), and DIPEA (8 eq.) were dissolved in 2 mL DMF, incubated for 5 min, and added to the deprotected resin. The resin coupled with the solution for 1 hr while shaking. The resin was washed with DMF (2 mL×3), then deprotected and coupled to the N$^\alpha$-Fmoc protected next amino acid (0.5 hr coupling time), and the process repeated for the remaining amino acids. The final amino acid was N$^\alpha$-Boc-protected instead of N$^\alpha$-Fmoc protected. Proceeding from the final coupling, the resin was washed with DMF (2 mL×3) then DCM (2 mL×3).

Next, 4-nitrophenylchloroformate (4 eq.) was dissolved in 2 mL of DCM and then added to the resin and shaken for 30 min. The solution was drained and an additional 2 mL of 4-nitrophenylchloroformate in DCM was added to resin and shaken for another 30 min. After washing with DCM (2 mL×3), the resin was incubated with shaking with 5.5% DIPEA in DMF (2 mL×3, 10 min per round). After the final incubation, the resin was washed with DMF (2 mL×3), DCM (2 mL×3), and then Et$_2$O (2 mL×3). The washed resin was dried under N$_2$ and then under vacuum. The peptide was simultaneously deprotected and cleaved from the resin using 2 mL of 90/5/2.5/2.5 TFA/DCM/H$_2$O/triisopropylsilane (TIPS) solution while shaking for 2 hr. The solution was filtered from the resin, then the resin was washed with another 2 mL of the cleavage solution and filtered again. The solution was mixed with 40 mL of Et$_2$O, chilled at −20° C. for at least 1 hr, then centrifuged using a Beckman-Coulter Allegra 6R with a GH-3.8 rotor at 3500 rpm for 30 min at 4° C. The supernatant was decanted, and the pellet dissolved in 6 mL of 25% ACN in H$_2$O and lyophilized.

The crude, lyophilized peptide was reconstituted in 25% ACN in H$_2$O, passed through a 0.22 μm filter, and purified by RP-HPLC. Fractions were collected and analyzed using MALDI-MS, and those with peaks matching that of the linear peptides were kept and lyophilized. Purified linear peptides were cyclized in 3 mL of cyclization buffer (20% ACN, 80% 6 M guanidinium chloride in 0.1 M Na$_2$PO$_4$, pH 6.8) for 2 hr at 50° C. with shaking. Following cyclization, solutions were passed through 0.22 μm filter, diluted with 1 mL of H$_2$O, and purified by RP-HPLC. Fractions were again analyzed with MALDI-MS to identify those with cyclized peptide, and those fractions were submitted for high-resolution mass measurement and analytical RP-HPLC to assess final purity.

Acetylated AIP analog peptide synthesis. Synthesis of AIP analogs with an acetylated N-terminus follows the same protocol of standard AIP synthesis as above with the exception of the final amino acid coupling (FIG. 3). Instead of a N$^\alpha$-Boc-protected amino acid, a standard Na-Fmoc-protected amino acid was used. After this coupling, the resin was washed with DMF (2 mL×3), and the Fmoc group was deprotected using 20% piperidine (2 mL×3 for 5, 5, and 10 min). Next, acetic anhydride (10 eq.) and DIPEA (7 eq.) were dissolved in 2 mL of DMF and added to the resin to shake for 15 min. The resin was then washed with DMF (2 mL×3) and DCM (2 mL×3). After this point, the synthesis followed the protocol for standard AIP analogs beginning at the addition of 4-nitrophenylchloroformate.

AIP amide peptide synthesis. AIP analogs where the thioester bond is replaced with an amide linkage, as were synthesized on pre-loaded L-valine 2-chlorotrityl resin (0.74 mmol/g) using standard Fmoc/tBu procedures and adapted from previous reports (FIG. 4).[55] Approximately 50 mg of resin (0.037 mmol, 1 eq.) was swelled in DCM for 40 min in a reaction vessel. Resin was then washed with DMF (2 mL×3), then the next amino acid was prepared above. Rest of linear synthesis followed protocol for standard AIP synthesis, with the exception of using longer coupling times (all amino acids coupled for at least 1 hr) and then using N$^\alpha$-Fmoc-N$^\beta$-4-Mtt-diaminopropionic acid (Dap) or its D-amino acid equivalent for amide linkages instead of the usual N$^\alpha$-Fmoc-S-Trt-cysteine for the appropriate linkage amino acid. After the final N$^\alpha$-Boc-protected amino acid was coupled, the resin was washed with DMF (2 mL×3) and then DCM (2 mL×3).

Then, to facilitate partial deprotection and cleavage from the resin, 2 mL of 2% TFA, 2% TIPS in DCM was added to the resin and shaken for 2 min, the solution collected in a 50 mL round-bottom flask, and the process repeated four more times. The resin was washed with DCM (2 mL×3), and the solution collected in the same round-bottom flask. The solvent was removed using a rotary evaporator, leaving an oil. The oil was dissolved in 3 mL of ACN, then diluted with 3 mL of H$_2$O and lyophilized. To cyclize the partially deprotected peptide, PyAOP (2 eq.) and DIPEA (4 eq.) were dissolved in 5 mL of DCM and added to the lyophilized peptide and stirred for 24 hr at RT. The solvent was removed using rotary evaporation, leaving an oil.

To fully deprotect the peptide, 5 mL of a 90/5/2.5/2.5 TFA/DCM/H$_2$O/TIPS solution was added to the round-bottom flask and stirred for 2 hr. The solution was then transferred to a 50 mL falcon tube and mixed with 40 mL of cold Et$_2$O and chilled in a −20° C. freezer overnight to precipitate. The peptide was centrifuged following the standard AIP synthesis protocol, the solvent decanted, and the pellet dissolved in 50% ACN in H$_2$O and lyophilized. The lyophilized peptide was reconstituted in 25% ACN in H$_2$O and purified by RP-HPLC. MALDI-MS confirmed which fractions contained desired peptides, and these fractions were submitted for high-resolution mass measurement and analytical RP-HPLC to confirm purity.

TABLE 3

MS spectral data, HPLC retention times, and purity data.

| Peptide | Calculated m/z [M + H]$^+$ (Da) | Observed m/z [M + H]$^+$ (Da) | Δm (ppm) | Retention time (min) | HPLC trace purity (%, 220 nm) |
| --- | --- | --- | --- | --- | --- |
| Ac-5-mer | 670.2728 | 670.2725 | 0.4 | 26.69 | 96.9 |
| AIP | 699.2993 | 699.2997 | 0.6 | 22.59 | >99 |
| 7-mer | 827.3943 | 827.394 | 0.4 | 22.37 | 97.7 |
| 8-mer | 914.4263 | 914.4276 | 1.4 | 20.95 | 92.3 |
| 9-mer | 1045.4668 | 1045.4679 | 1.1 | 21.25 | 94.3 |
| 10-mer | 566.753 $^a$ | 566.7532 $^a$ | 0.4 | 21.16 | 93.2 |
| 11-mer | 610.2691 $^a$ | 610.2682 $^a$ | 1.5 | 20.94 | 97.9 |
| 12-mer | 667.7825 $^a$ | 667.7828 $^a$ | 0.4 | 20.86 | 98.4 |
| 13-mer | 703.3011 $^a$ | 703.3015 $^a$ | 0.6 | 20.78 | 96.5 |
| 14-mer | 752.8353 $^a$ | 752.8357 $^a$ | 0.5 | 20.89 | 98.2 |
| 15-mer | 816.8828 $^a$ | 816.8826 $^a$ | 0.2 | 20.28 | 96.4 |
| AIP F3A | 623.268 | 623.2679 | 0.2 | 20.35 | 99.0 |
| AIP M4A | 661.2779 | 611.2774 | 0.8 | 21.39 | >99 |
| AIP F5A | 623.268 | 623.2684 | 0.6 | 19.50 | 99.0 |
| AIP V6A | 671.268 | 671.2682 | 0.3 | 21.04 | 98.8 |
| AIP A1dA | 699.2993 | 699.2998 | 0.7 | 22.74 | 97.5 |
| AIP C2dC | 699.2993 | 699.2995 | 0.3 | 22.19 | 97.9 |
| AIP F3dF | 699.2993 | 699.2996 | 0.4 | 21.78 | 98.2 |
| AIP M4dM | 699.2993 | 699.2993 | <0.1 | 22.24 | 96.2 |
| AIP F5dF | 699.2993 | 699.2999 | 0.9 | 22.04 | 96.2 |
| AIP V6dV | 699.2993 | 699.2995 | 0.3 | 22.14 | 98.1 |
| AIP A1P | 725.315 | 725.3145 | 0.7 | 23.09 | 98.6 |
| AIP A1T | 729.3099 | 729.3099 | <0.1 | 22.45 | 98.6 |
| AIP A1K | 756.3572 | 756.3572 | <0.1 | 26.07 | 98.6 |
| AIP A1V | 727.3306 | 727.3315 | 1.2 | 28.34 | 96.5 |
| AIP C2Dap (AIP amide) | 682.3381 | 682.3381 | <0.1 | 22.25 | 95.2 |
| AIP C2dDap (AIP D-amide) | 682.33813 | 682.3386 | 0.7 | 25.90 | 96.2 |
| AIP F3Y | 715.2942 | 715.2958 | 2.2 | 26.02 | 96.4 |
| AIP F3L | 665.315 | 665.3159 | 1.4 | 27.28 | 98.3 |
| AIP F3H | 689.2898 | 689.2892 | 0.9 | 18.74 | 95.4 |
| AIP F3S | 639.2629 | 639.2628 | 0.2 | 19.70 | 97.0 |
| AIP F3W | 738.3102 | 738.3089 | 1.8 | 22.57 | 98.8 |
| AIP M4dA | 639.2959 | 639.2967 | 1.3 | 26.04 | 96.4 |
| AIP F5Y | 715.2942 | 715.2959 | 2.4 | 25.26 | 98.6 |
| AIP F5L | 665.315 | 665.3149 | 0.2 | 22.22 | 96.4 |
| AIP F5H | 689.2898 | 689.2899 | 0.1 | 22.05 | 97.8 |
| AIP F5W | 738.3102 | 738.3112 | 1.4 | 22.25 | >99 |
| AIP A1K/C2dC | 756.3572 | 756.3574 | 0.3 | 25.59 | 97.3 |
| AIP A1K/M4dM | 756.3572 | 756.357 | 0.3 | 25.87 | 97.4 |
| AIP C2dC/M4dM | 699.2993 | 699.2999 | 0.9 | 26.96 | 97.0 |
| AIP A1K/C2dC/M4dM | 756.3572 | 756.3568 | 0.5 | 25.45 | 98.5 |
| 7-mer A2K | 884.4521 | 884.452 | 0.1 | 19.91 | >99 |
| 7-mer C3dC | 827.3943 | 827.3937 | 0.7 | 25.22 | 97.3 |
| 7-mer M5dM | 827.3943 | 827.3937 | 0.7 | 20.76 | 98.2 |
| 7-mer C3dC/M5dM | 827.3943 | 827.3939 | 0.5 | 20.23 | >99 |
| *L. grandensis* tr AIP | 548.25373 | 548.2532 | 1.0 | 25.72 | 98.4 |
| *L. grayi* AIP | 611.2316 | 611.232 | 0.7 | 22.98 | >99 |
| *L. kieliensis* AIP | 547.2545 | 547.2541 | 0.7 | 19.35 | >99 |
| *L. newyorkensis* AIP | 711.3535 $^b$ | 711.3535 $^b$ | <0.1 | 29.12 | >99 |
| *L. weihenstephanensis* AIP | 653.3439 | 653.3436 | 0.5 | 21.29 | >99 |

$^a$ Mass calculated and observed as [M + 2H]$^{2+}$.
$^b$ Mass calculated and observed as [M + Na]$^+$.

Example 3

Figures 5A, 5B:
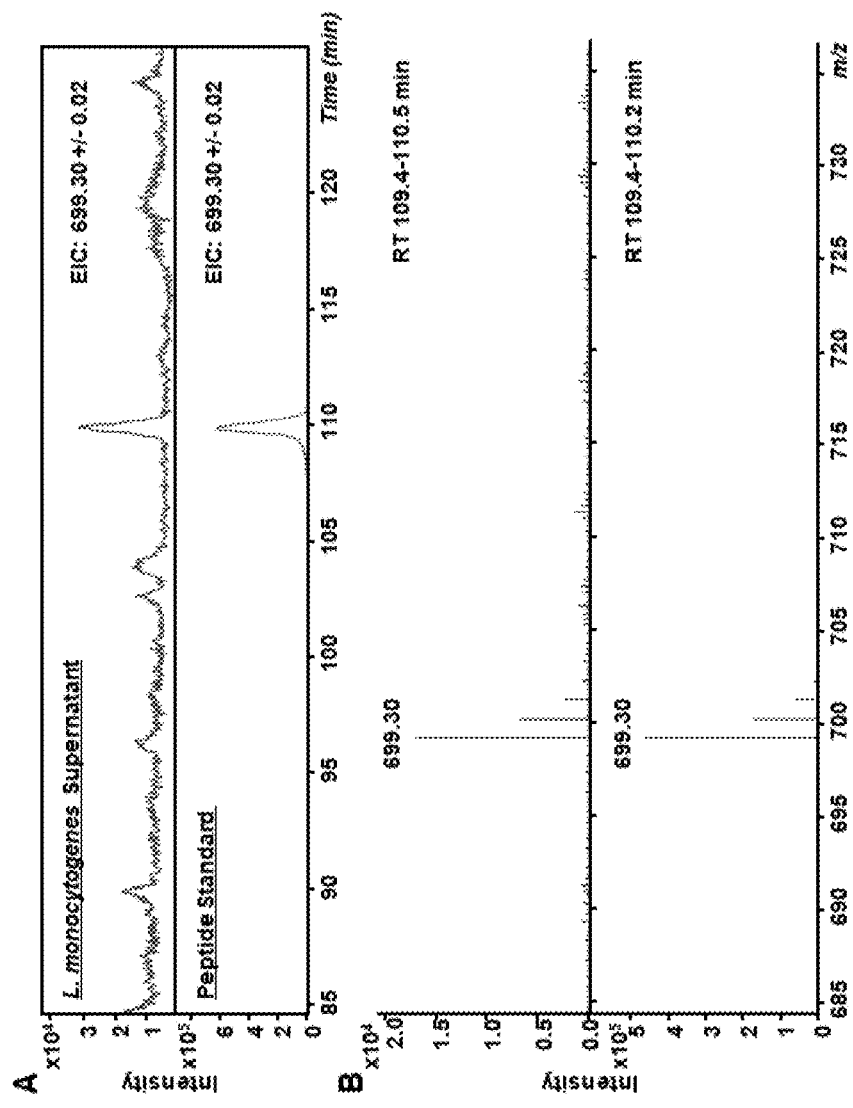
FIGS. 5A and 5B show LC-MS results demonstrating the presence of native AIP in *L. monocytogenes* supernatant.
Figure 6:
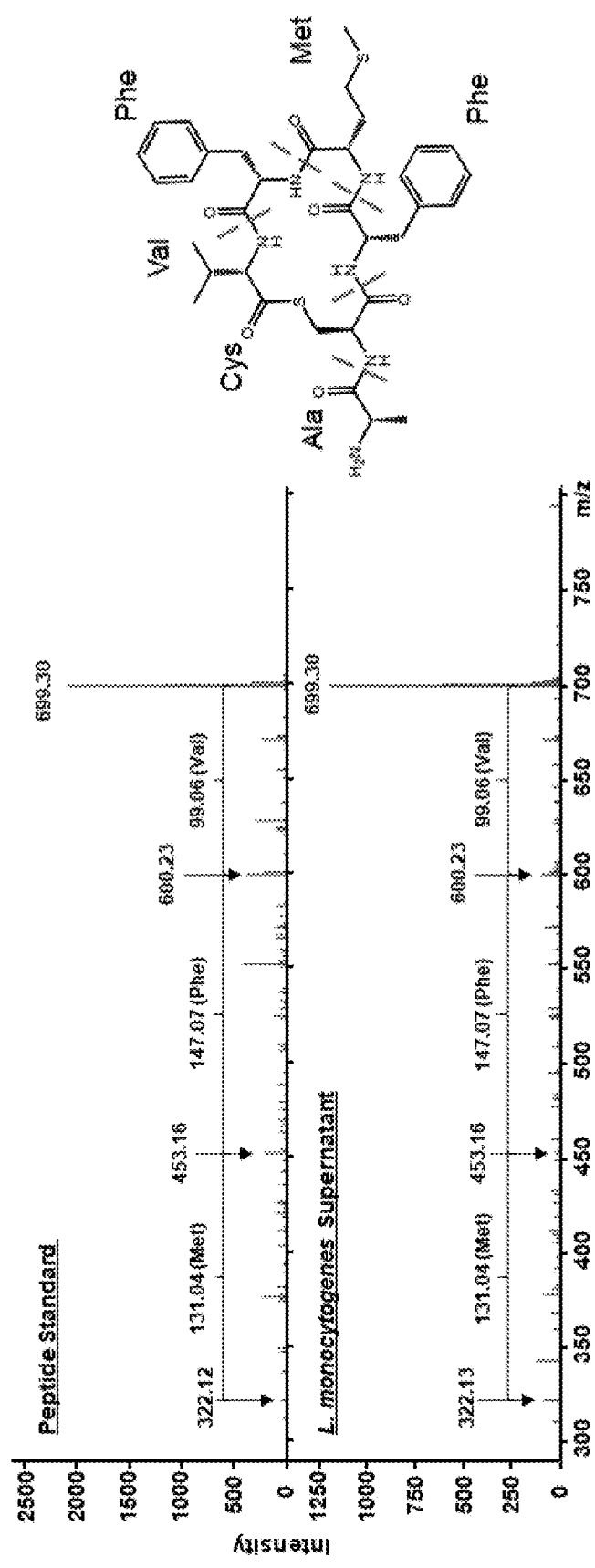
FIG. 6 shows LC-MS/MS results demonstrating that the fragmentation of the native AIP in *L. monocytogenes* supernatant matches that of the 6-mer standard. MS/MS spectra for the 6-mer peptide standard (top, energy 23 eV, RT 110.4 min) and the native AIP from *L. monocytogenes* supernatant (bottom, energy 20 eV, RT 110.0 min). Figure discloses SEQ ID NO: 1.

Native AIP Isolation and Characterization. Overnight cultures of *L. monocytogenes* EGD-e were grown in BHI, centrifuged at 3000 rpm for 15 min at 4° C., and 5 mL of the supernatant were lyophilized. A scoop of lyophilized supernatant was re-constituted in 1.5 mL of 18 MS2 water, vortexed, chilled at 4° C. for one hour, then centrifuged at 15000 rpm for 10 min. The supernatant was removed, and the pellet was reconstituted in 25% acetonitrile in water with 0.1% formic acid for injection on an LC-MS/MS instrument. For comparison, peptide standards (prepared per Example 2) were diluted in 25% acetonitrile in water with 0.1% formic acid and injected on the instrument. FIG. 5 shows LC-MS (extracted ion chromatograms) of 699.30+/−0.2 m/z for the wild-type (WT) supernatant (top) and peptide standard mixture (bottom). FIG. 5B shows mass spectra averaged over the peak retention time (RT) for WT (top) and peptide standard mixture (bottom). FIG. 6 shows LC-MS/MS fragmentation of the native AIP in *L. monocytogenes* supernatant matches with that of the 6-mer standard. MS/MS spectra for the 6-mer peptide standard (top, energy 23 eV, RT 110.4 min) and the native AIP from *L. monocytogenes* supernatant (bottom, energy 20 eV, RT 110.0 min). These results demonstrate that the 6-mer peptide (hereby referred to as the native AIP, A-(C-F-M-F-V) (SEQ ID NO: 1) from the supernatant of wild-type *L. monocytogenes*, in agreement with the structure proposed by Todd et al.[35] rather than a structure with a different exocyclic tail.[34]

Example 4

Non-cognate AIP activity. A variety of putative AIP compounds from other *Listeria* species (*L. grandensis*, *L. grayi*, *L. kieliensis*, *L. newyorkensis*, *L. weihenstephanensis*) and other gram-positive bacterial species (*Staphylococcus aureus* and *S. epidermidis*) were prepared as discussed in Example 2 and tested for QS activity in Lm using the fluorescence reporter assay described above (see Materials and General Methods). Results are presented in Table 4.

TABLE 4

Agonism and antagonism activity of native and putative AIPs and AIP analogs of other species against *L. monocytogenes* AgrC.

| Compound | Sequence | $EC_{50}$ (nM) | Max Activation (%) | $IC_{50}$ (nM) | Max Inhibition (%) |
|---|---|---|---|---|---|
| Lm AIP | A-(C-F-M-F-V) | 29.6 | 114 | —[a] | 2.66 |
| Lm AIP F3S | A-(C-S-M-F-V) | —[a] | 16.1 | —[a] | 16.3 |
| Lm AIP V6A | A-(C-F-M-F-A) | 241 | 69.0 | —[a] | 15.0 |
| Sa AIP-I | Y-S-T-(C-D-F-I-M) | —[b] | 12.2 | —[b] | 1.29 |
| Sa AIP-II | G-V-N-A-(C-S-S-L-F) | —[b] | 12.0 | —[b] | 0 |
| Sa AIP-III | I-N-(C-D-F-L-L) | —[b] | 11.3 | —[b] | 0.64 |
| Sa AIP-IV | Y-S-T-(C-Y-F-I-M) | —[b] | 9.81 | —[b] | 8.56 |
| Sa AIP-III D4A | I-N-(C-A-F-L-L) | —[b] | 12.3 | —[b] | 5.87 |
| Se AIP-I | D-S-V-(C-A-S-Y-F) | —[b] | 8.65 | —[b] | 0 |
| Se AIP-II | N-A-S-K-Y-N-P-(C-S-N-Y-L) | —[b] | 8.45 | —[b] | 0 |
| Se AIP-III | N-A-A-K-Y-N-P-(C-A-S-Y-L) | —[b] | 8.73 | —[b] | 0 |
| Se AIP-I D1AS6A | A-S-V-(C-A-A-Y-F) | —[b] | 12.4 | —[b] | 0 |
| Se AIP-I D1AV3AS6A | A-S-A-(C-A-A-Y-F) | —[b] | 12.1 | —[b] | 0.06 |
| *L. grandensis* tr AIP | Ac-(C-V-G-F-V) | —[a] | 10.1 | —[b] | 0 |
| *L. grayi* AIP | A-(C-S-M-F-A) | —[b] | 10.7 | —[a] | 0.42 |
| *L. kieliensis* AIP | S-(C-V-G-L-S) | —[b] | 10.4 | —[b] | 0 |
| *L. newyorkensis* AIP | S-(C-F-L-I-F) | —[b] | 23.6 | —[b] | 0.96 |
| *L. weihenstephanensis* AIP | S-(C-V-L-H-L) | —[b] | 11.2 | —[b] | 0 |

[a] Curve not converged.
[b] From single point data only, no potency data available.
Activation values normalized with 1 µM *L. monocytogenes* AIP (100%) and media (0%) controls in ΔagrD reporter.
Inhibition values normalized with media (100%) and vehicle (0%) controls in wild-type reporter.
Lm = *L. monocytogenes*; Sa = *Staphylococcus aureus*; Se = *S. epidermidis*.

Non-cognate AIP activity. In other Gram-positive bacteria, native AIPs from different strains and species often have cross-activity on non-self AgrC receptors.[56-59] While some of the *Staphylococci* species have multiple agr specificity groups,[56, 60] there have not been any reports of such divergence in any individual *Listeria* species.[61] The *Listeria* genus is split into two clades, *Listeria sensu stricto* and *Listeria sensu lato*.[62-63] All the species within *Listeria sensu stricto*, including *L. monocytogenes*, share a well-conserved AgrD sequence and most notably an identical sequence surrounding the conserved cysteine in the AIP region. However, the genomic data available for *Listeria sensu lato*, which are generally believed to be more docile species, shows these members all have relatively distinct AgrD sequences. Peptides corresponding to putative AIPs from each of the *Listeria* species were prepared as described in Example 2, assuming an identical five-membered macrocycle and exocyclic tail length (with the exception of *L. grandensis* due to synthetic difficulties due to the exocyclic cysteine, instead using the truncated peptide). These compounds were screened these against the *L. monocytogenes* reporter strains described in Example 1. For comparison, the native AIPs and some AIP analogs from *S. aureus* and *S. epidermidis* were also screened.[64, 65]

None of the putative AIPs from other *Listeria* species nor any of the *Staphylococci*-based AIPs showed excellent activity. All but two of the peptides were devoid of any observable agonism or antagonism activity compared to vehicle, and the two remaining peptides (*S. aureus* AIP-IV and *L. newyorkensis* AIP) had minimal efficacy at 10 µM (FIG. 1B). This selectivity was unexpected. Thus, while it is well-established that *Staphylococci* AgrCs are generally capable of binding structurally diverse non-cognate AIPs as evidenced by the myriad of peptide inhibitors,[66] the *L. monocytogenes* AgrC does not appear to readily accommodate peptides that differ from its cognate AIP.

Example 5

Figures 7A, 7B:
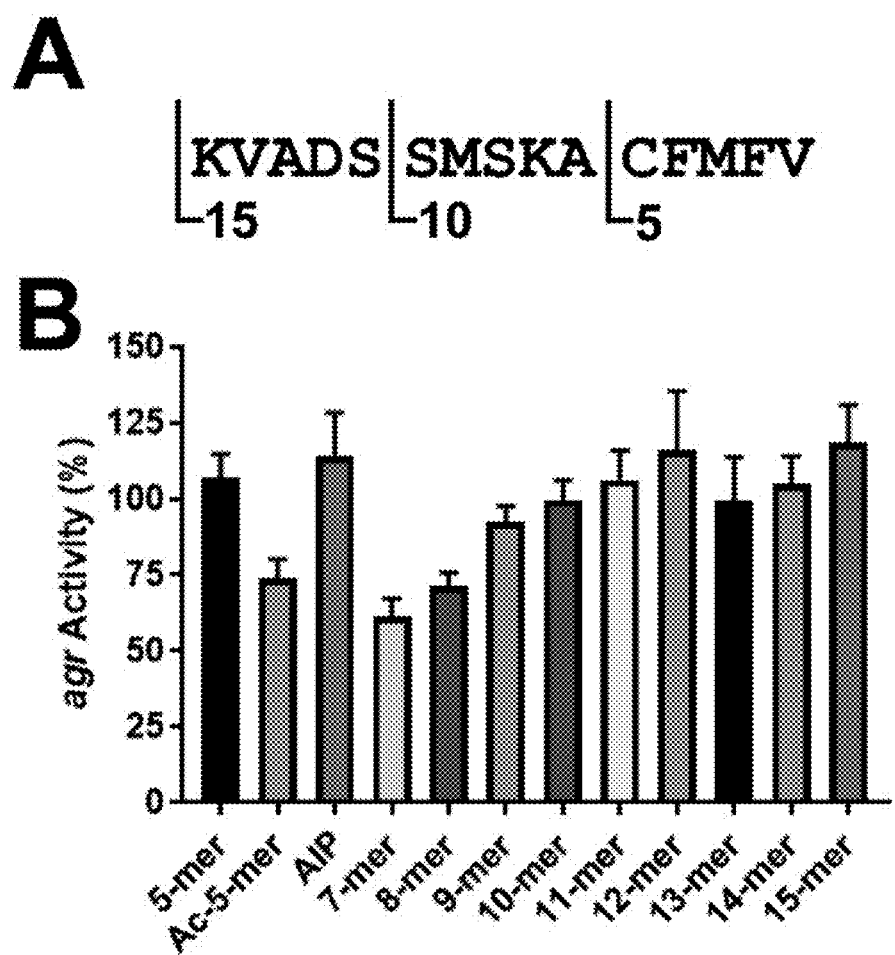
FIGS. 7A and 7B show effects of tail-length modifications of AIP.

QS by exocyclic analogs of Lm AIP. A series of compounds of varying lengths based on the *L. monocytogenes* AgrD amino acid sequence (FIG. 7A) were prepared in accordance with Example 2 and tested for QS activity in Lm using the fluorescence reporter assay described above (see Materials and General Methods). Results are presented in Table 5 and FIG. 7B.

TABLE 5

Agonism and antagonism activity of *L. monocytogenes* AIP analogs with varying exocyclic tail length.

| Compound | Sequence | $EC_{50}$ (nM) | Max Activation (%) | $IC_{50}$ (nM) | Max Inhibition (%) |
|---|---|---|---|---|---|
| AIP | A-(C-F-M-F-V) | 29.7 | 114 | —[a] | 2.66 |
| 5-mer | (C-F-M-F-V) | 260 | 110 | —[a] | 0 |
| Ac-5-mer | Ac-(C-F-M-F-V) | 46.3 | 75.3 | —[a] | 6.39 |
| 7-mer | K-A-(C-F-M-F-V) | 61.7 | 64.6 | 866 | 38.3 |
| 8-mer | S-K-A-(C-F-M-F-V) | 68.6 | 71.5 | 842 | 29.4 |
| 9-mer | M-S-K-A-(C-F-M-F-V) | 23.5 | 93.6 | 416 | 8.89 |
| 10-mer | S-M-S-K-A-(C-F-M-F-V) | 21.5 | 110 | —[a] | 0 |
| 11-mer | S-S-M-S-K-A-(C-F-M-F-V) | 14.3 | 111 | —[a] | 3.90 |
| 12-mer | D-S-S-M-S-K-A-(C-F-M-F-V) | 43.4 | 116 | —[a] | 0.26 |
| 13-mer | A-D-S-S-M-S-K-A-(C-F-M-F-V) | 29.0 | 108 | —[a] | 0 |
| 14-mer | V-A-D-S-S-M-S-K-A-(C-F-M-F-V) | 39.9 | 105 | —[a] | 0 |
| 15-mer | K-V-A-D-S-S-M-S-K-A-(C-F-M-F-V) | 22.2 | 122 | —[a] | 0.23 |

[a]Curve not converged.
Activation values normalized with 1 μM AIP (100%) and media (0%) controls in ΔagrD reporter.
Inhibition values normalized with media (100%) and vehicle (0%) controls in wild-type reporter.

Altering the AIP exocyclic tail length causes only minor effects on activity. Previous SAR studies of AIPs in other organisms have found that changing or removing the exocyclic tail length of the native AIP can have dramatic results on activity, e.g., mode-switching agonists to antagonists of varying potency.[40-42] The results shown in FIG. 7B and Table 5 with the agr-GFP reporters of Example 1 demonstrate that tail length changes had negligible effects on potency and all analogs maintained substantial agonism activity.

Unlike truncated AIPs in other organisms that often produce low potency antagonists,[12, 40-43] the truncated *L. monocytogenes* AIP (5-mer) fully maintained its agonism activity. However, the apparent potency dropped ten-fold. An acetylated N-terminus analog slightly reduced maximal activation but restored the potency. Similarly, elongating the AIP to 7- or 8-amino acids lowered activation while maintaining potency; however, further elongation largely restored activity relative to the native AIP.

Example 6

Alanine and D-Amino Acid Analogs. Analogs in which each amino acid was replaced with alanine with the exception of Ala1 and Cys2 (as it is involved in macrocycle formation) or with a D-amino acid were prepared as described in Example 2. These compounds were tested for QS activity in Lm using the fluorescence reporter assay described above (see Materials and General Methods). Results are presented in Table 6.

TABLE 6

Reporter assay activity data for alanine and D-amino acid scan analogs of *L. monocytogenes* AIP.

| Compound | Sequence | $EC_{50}$ (nM) | Max Activation Observed (%)[a] | $IC_{50}$ (nM) | Max Inhibition Observed (%)[b] |
|---|---|---|---|---|---|
| AIP[c] | A-(C-F-M-F-V) | 29.7 | 114[c] | —[d] | NA[e] |
| AIP F3A | A-(C-A-M-F-V) | —[d] | 9.72 | —[d] | 3.65 |
| AIP M4A | A-(C-F-A-F-V) | 1980 | 53.5 | —[d] | 7.85 |
| AIP F5A | A-(C-F-M-A-V) | —[d] | 6.37 | —[d] | NA[e] |
| AIP V6A | A-(C-F-M-F-A) | 241 | 69.0 | —[d] | 15.0 |
| AIP A1dA | dA-(C-F-M-F-V) | 96.9 | 58.8 | —[d] | 15.2 |
| AIP C2dC | A-(dC-F-M-F-V) | 106 | 41.0 | 3970 | 48.4 |
| AIP F3dF | A-(C-dF-M-F-V) | —[d] | 6.63 | —[d] | 14.7 |
| AIP M4dM | A-(C-F-dM-F-V) | 10.2 | 111 | —[d] | 3.99 |

TABLE 6-continued

Reporter assay activity data for alanine and D-amino acid scan analogs of L. monocytogenes AIP.

| Compound | Sequence | $EC_{50}$ (nM) | Max Activation Observed (%)[a] | $IC_{50}$ (nM) | Max Inhibition Observed (%)[b] |
|---|---|---|---|---|---|
| AIP F5dF | A-(C-F-M-dF-V) | 2180 | 72.3 | —[d] | 2.71 |
| AIP V6dV | A-(C-F-M-F-dV) | 883 | 72.9 | —[d] | NA[e] |

[a]Activation values normalized with 1 μM AIP (100%) and media (0%) controls in ΔagrD reporter.
[b]Inhibition values normalized with media (100%) and vehicle (0%) controls in wild-type reporter.
[c]Native AIP.
[d]Dose response did not converge.
[e]NA = not active.

Results and Discussion. The most notable alanine analogs were AIP F3A and AIP F5A, as these substitutions abolished agonism activity and had no noticeable antagonism. The lack of both agonism and antagonism activity suggests that these two peptides are unable to bind to their receptor effectively, indicating that Phe3 and Phe5 likely play a critical role in AIP-AgrC binding. The remaining two alanine substitutions, AIP M4A and AIP V6A, both exhibited decreased potency and agonism compared to the native AIP suggesting that although these side chains contribute to full activation of AgrC, these positions tolerate a variety of other side chains.

Results from analogs with D-amino acids show how stereochemical inversion influenced peptide activity. AIP F3dF was largely inactive in both agonism and antagonism screens. Similarly, while AIP F5dF did maintain some agonism activity, a two orders of magnitude loss in potency was observed. These results further support an important role for both phenylalanine residues in AIP-AgrC binding. The effects of D-amino acid substitution were better tolerated at Ala1 and Val6, although both did still see losses in efficacy and potency. Inverting the remaining two positions gave surprising outcomes. First, by inverting the stereochemistry of Cys2 and therefore the orientation of the thiolactone bridge, the resulting peptide AIP C2dC lost a substantial amount of agonism activity with a modest three-fold loss in potency in the ΔagrD reporter. Moreover, AIP C2dC was able to inhibit the wild-type reporter to 50% of its maximum activity, the most substantial reduction seen thus far. Second, while all substitutions explored so far have had either negligible or negative effects on potency, the incorporation of D-Met increased the potency three-fold with no effect on agonism for AIP M4dM, showing that the stereochemistry of Cys2AgrC heavily influences AgrC agonism.

Example 7

Further compounds of the present technology were synthesized as described in Example 2 and screened in the wild-type and ΔagrD reporters as described above. Results are presented in Table 7.

TABLE 7

Reporter assay activity data for compounds of the present technology.

| Compound | Sequence | $EC_{50}$ (nM) | Max Activation Observed (%)[a] | $IC_{50}$ (nM) | Max Inhibition Observed (%)[b] |
|---|---|---|---|---|---|
| AIP[c] | A-(C-F-M-F-V) | 29.7 | 114 | —[d] | NA[e] |
| First Generation Analogs | | | | | |
| AIP A1P | P-(C-F-M-F-V) | 29.0 | 76.8 | 611 | 23.7 |
| AIP A1T | T-(C-F-M-F-V) | 35.2 | 88.1 | 420 | 11.7 |
| AIP A1K | K-(C-F-M-F-V) | 22.9 | 80.0 | 233 | 31.3 |
| AIP A1V | V-(C-F-M-F-V) | 7.67 | 109 | —[d] | 1.63 |
| AIP C2Dap | A-(Dap-F-M-F-V) | 342 | 92.9 | —[d] | 5.32 |
| AIP C2dDap | A-(Dap-F-M-F-V) | —[d] | 14.3 | —[d] | 19.3 |
| AIP F3Y | A-(C-Y-M-F-V) | 518 | 47.4 | 3460 | 33.4 |
| AIP F3L | A-(C-L-M-F-V) | 693 | 37.6 | 3600 | 33.4 |
| AIP F3H | A-(C-H-M-F-V) | —[d] | 12.4 | —[d] | 24.9 |
| AIP F3W | A-(C-W-M-F-V) | 414 | 60.6 | 2180 | 27.1 |
| AIP M4dA | A-(C-F-dA-F-V) | 455 | 82.0 | —[d] | 9.54 |
| AIP F5Y | A-(C-F-M-Y-V) | 5620 | 44.4 | —[d] | 6.61 |
| AIP F5L | A-(C-F-M-L-V) | 2060 | 64.8 | —[d] | 8.97 |
| AIP F5H | A-(C-F-M-H-V) | —[d] | 7.13 | —[d] | 2.19 |
| AIP F5W | A-(C-F-M-W-V) | 1130 | 85.8 | —[d] | 8.43 |
| Second Generation Analogs | | | | | |
| AIP A1K/C2dC | K-(dC-F-M-F-V) | —[d] | 10.2 | 4440 | 30.7 |
| AIP A1K/M4dM | K-(C-F-dM-F-V) | 4.18 | 74.1 | —[d] | 20.2 |
| AIP C2dC/M4dM | A-(dC-F-dM-F-V) | 24.1 | 35.7 | 242 | 64.8 |
| A1K/C2dC/M4dM | K-(dC-F-dM-F-V) | —[d] | 8.10 | 1770 | 88.6 |
| 7-mer A2K | K-K-(C-F-M-F-V) | 185 | 64.8 | 359 | 51.8 |
| 7-mer C3dC | K-A-(dC-F-M-F-V) | —[a] | 7.08 | 3800 | 49.3 |

TABLE 7-continued

Reporter assay activity data for compounds of the present technology.

| Compound | Sequence | $EC_{50}$ (nM) | Max Activation Observed (%)[a] | $IC_{50}$ (nM) | Max Inhibition Observed (%)[b] |
|---|---|---|---|---|---|
| 7-mer M5dM | K-A-(C-F-dM-F-V) | 8.29 | 71.9 | —[a] | 18.5 |
| 7-mer C3dC/M5dM | K-A-(dC-F-dM-F-V) | —[a] | 7.89 | 1290 | 88.9 |

[a]Activation values normalized with 1 μM AIP (100%) and media (0%) controls in ΔagrD reporter.
[b]Inhibition values normalized with media (100%) and vehicle (0%) controls in wild-type reporter. See methods.
[c]Native AIP.
[d]Dose response did not converge.
[e]NA = not active.

Results and Discussion. Four analogs with substitutions of the exocyclic residue Ala1 with varying polarity, charge, and steric bulk were prepared. Three of the analogs—AIP A1P, AIP A1T, and AIP A1K—were partial agonists with slightly diminished agonistic activity. The remaining analog, AIP A1V, maintained the full activity of the parent AIP with enhanced potency similar to AIP M4dM. The relatively minor activity changes despite rather disparate side chain properties suggests this exocyclic position is quite tolerant to substitution.

Analogs at Phe3 and Phe5 were prepared and tested. Bulky and hydrophobic substitutions (tyrosine, leucine, tryptophan) in the Phe3 position performed more favorably than the alanine or D-phenylalanine substitutions. Nevertheless, these new analogs were still poor partial agonists (agonism activity cut substantially and potency losses greater than 10-fold). Alternatively, replacement of Phe3 with histidine completely abolished any observable agonism. The same substitutions were also examined in Phe5, which acted similarly in terms of activity but had even more severe losses in potency.

Although substituting Met4 with L-alanine (AIP M4A) resulted in a poor agonist with an $EC_{50}$ in the low micromolar range, inverting the stereochemistry to D-alanine (AIP M4dA) improved potency about four-fold. A similar magnitude increase was seen from inverting the stereochemistry of Met4 in the AIP. This suggests the D-stereochemistry contributes greatly to the potency increase.

Analogs replacing the thioester with an amide were prepared. AIP C2Dap largely retains the activation activity of the native AIP but shows a 10-fold loss in potency. Stereochemical inversion of the amide (AIP C2dDap) slightly decreases agr activity in the wild-type reporter by approximately 20% at 10 μM, analogous to the activity of AIP C2dC. However, unlike AIP C2dC, there appears to be little or no agr activation in the ΔagrD reporter for AIP C2dDap at 10 μM, suggesting AIP C2dDap had lost what little agonism that AIP C2dC had.

Analogs combining two or three of the following substitutions were prepared. The A1K substitution, while only modestly inhibiting the wild-type reporter, maintains potent binding to AgrC in agonism assays. Conversely, the C2dC substitution was able to significantly antagonize agr activity at the cost of potency. Lastly, the M4dM substitution saw a three-fold potency enhancement in the native AIP with no significant change in agr activity. Some analogous substitutions using the 7-mer analog as a scaffold were prepared and displayed similar trends.

Figure 8:
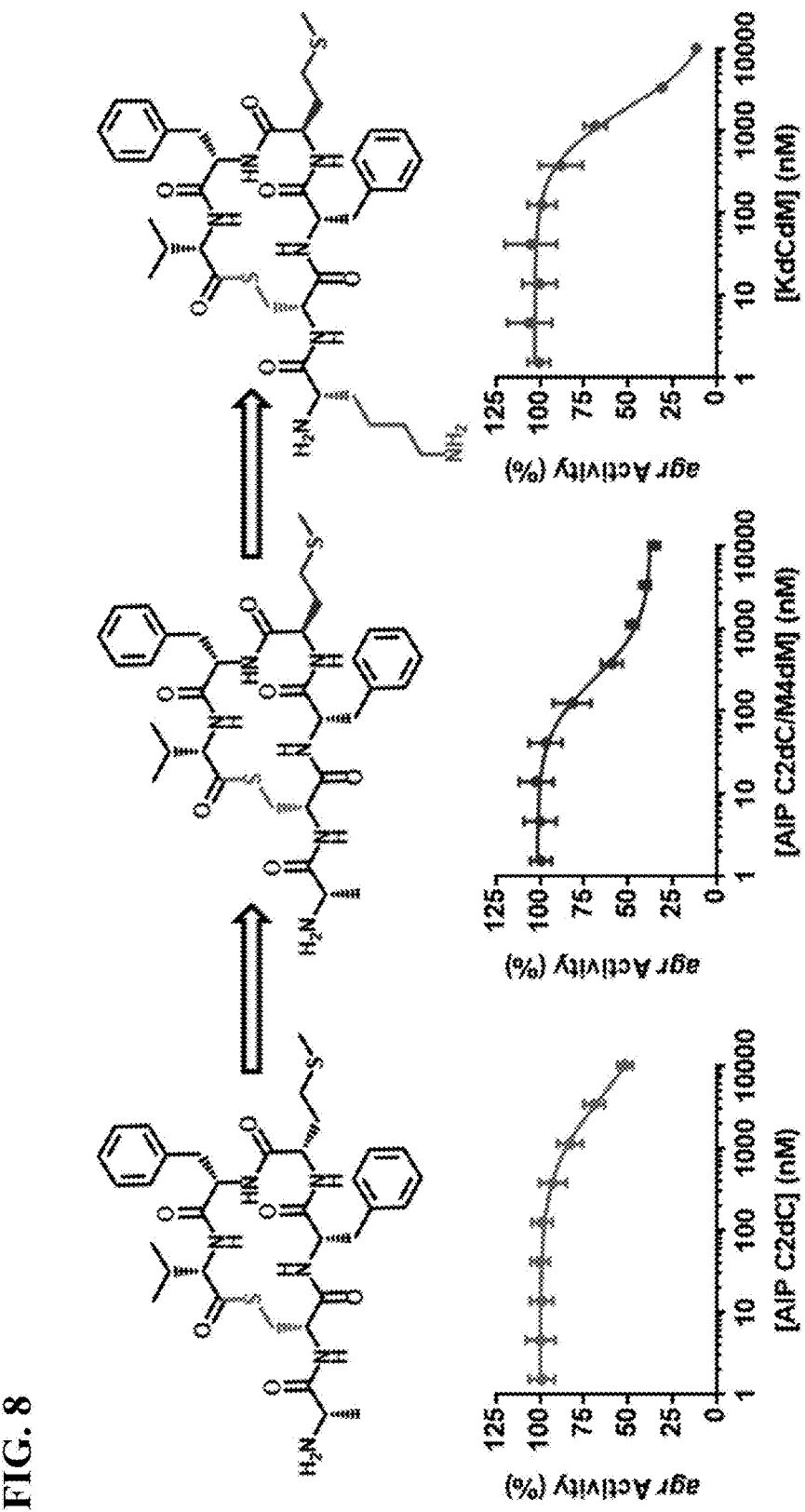
FIG. 8 shows dose response curves for illustrative compounds of the present technology that inhibit QS of wild-type reporter. Beginning with inhibitor AIP C2dC, additional substitutions M4dM and A1K contribute towards increased potency and inhibition respectively, culminating in the inhibitor KdCdM.

Combining the two inhibitory substitutions, A1K and C2dC, together resulted in an analog unable to agonize the ΔagrD reporter and showed significant inhibition in the wild-type assay. To improve potency, M4dM substitution was combined with the A1K and C2dC substitutions. Both AIP A1K/M4dM and AIP C2dC/M4dM saw significant improvements in their binding while maintaining the activity profile of their parent analogs containing L-methionine, further supporting the critical role D-methionine plays in increasing affinity for AgrC. These three features were combined into AIP A1K/C2dC/M4dM (hereafter referred to as KdCdM), resulting in the first analog capable of inhibiting wild-type activity to levels similar to basal ΔagrD activity (FIG. 8). Between the potency increase from the M4dM substitution and inhibition contributions from the A1K and C2dC substitutions, it appears each substitution independently adds to the activity of KdCdM.

Example 8

Figures 9A, 9B, 9C:
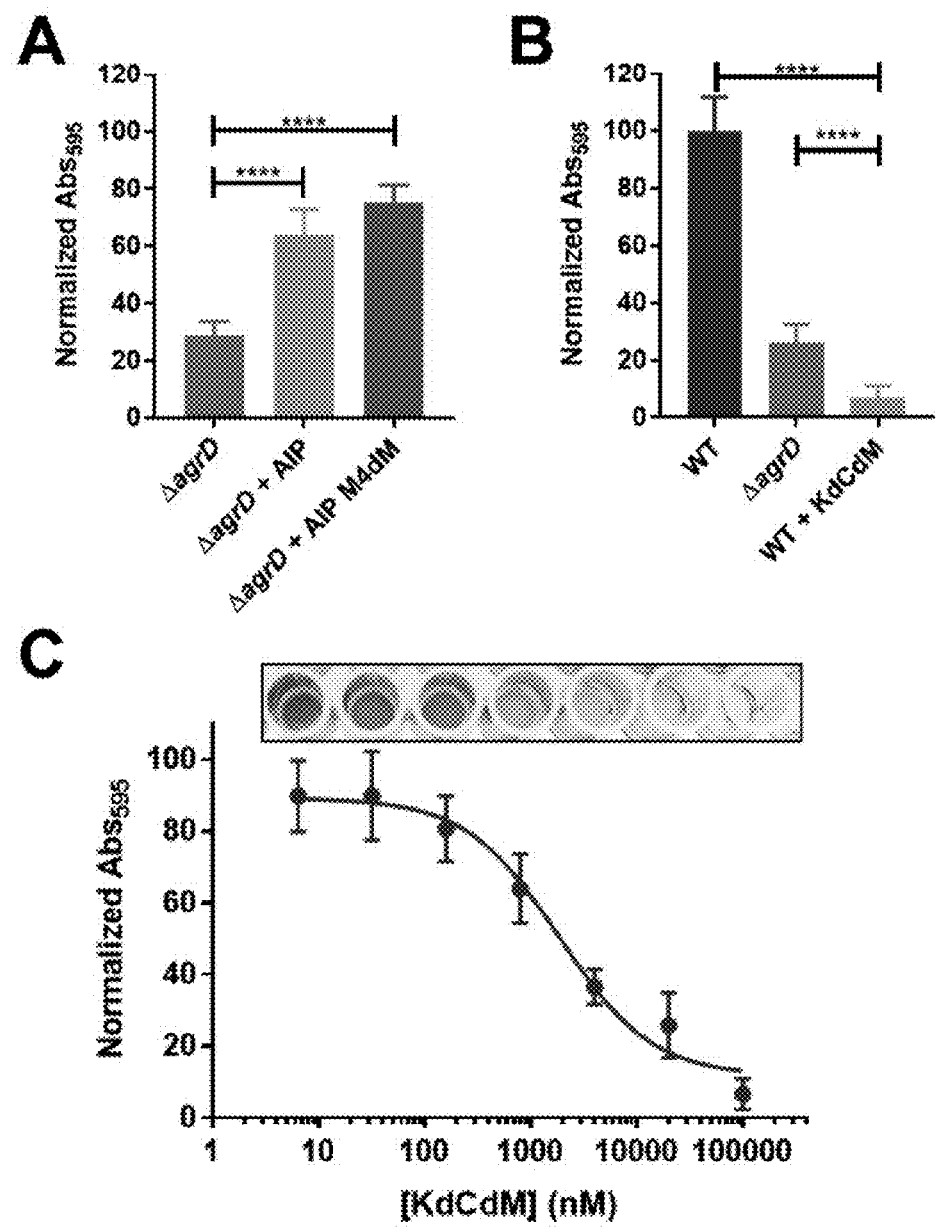
FIGS. 9A-9C show that an illustrative compound of the present technology can modulate biofilm formation depending on agr activity.

Modulation of Virulence Phenotypes with AIP analogs. Biofilm formation is a critical virulence phenotype that allows *L. monocytogenes* to persist and spread through harsh conditions, and attenuating biofilm formation has been a major focus in *L. monocytogenes* research.[46-47] Previous reports has noted a link between agr activity and biofilm formation in *L. monocytogenes*, as Δagr mutants have substantially attenuated adherence and biofilm formation on a variety of surfaces.[9, 33, 48-49] Compounds of the present technology were tested for restoration of biofilm formation in the ΔagrD strains, and reduction of biofilm formation in wild-type strains as described above (see Materials and Methods). Incubating ΔagrD bacteria with 10 μM native AIP or AIP M4dM doubled the biofilm production when compared to vehicle controls (FIG. 9A). On the other hand, wild-type biofilm formation was reduced by 90% when incubated with 100 μM of the most potent inhibitor, KdCdM (FIG. 9B). Moreover, this effect was dose-dependent (FIG. 9C) and revealed a nearly identical $IC_{50}$ value (1.86 μM) when compared to the fluorescence reporter data (1.77 μM). These biofilms assays demonstrate the potential for agr modulators to chemically control one of the most troublesome phenotypes of *L. monocytogenes*.

REFERENCES

1. Page, E. T., Trends in Food Recalls: 2004-13, EIB-191. U.S.D.A., Ed. Economic Research Service: 2018.
2. Scallan, E.; Hoekstra, R. M.; Angulo, F. J.; Tauxe, R. V.; Widdowson, M. A.; Roy, S. L.; Jones, J. L.; Griffin, P. M., Foodborne illness acquired in the United States—major pathogens. *Emerg Infect Dis* 2011, 17 (1), 7-15.
3. Radoshevich, L.; Cossart, P., *Listeria monocytogenes*: towards a complete picture of its physiology and pathogenesis. *Nat Rev Microbiol* 2018, 16 (1), 32-46.

4. Vivant, A. L.; Garmyn, D.; Piveteau, P., *Listeria monocytogenes*, a down-to-earth pathogen. *Front Cell Infect Microbiol* 2013, 3, 87.
5. Freitag, N. E.; Port, G. C.; Miner, M. D., *Listeria monocytogenes*—from saprophyte to intracellular pathogen. *Nat Rev Microbiol* 2009, 7 (9), 623-8.
6. Farber, J. M.; Peterkin, P. I., *Listeria monocytogenes*, a Food-Borne Pathogen. *Microbiol Rev* 1991, 55 (3), 476-511.
7. Gandhi, M.; Chikindas, M. L., *Listeria*: A foodborne pathogen that knows how to survive. *Int J Food Microbiol* 2007, 113 (1), 1-15.
8. Tilney, L. G.; Portnoy, D. A., Actin filaments and the growth, movement, and spread of the intracellular bacterial parasite, *Listeria monocytogenes*. *J Cell Biol* 1989, 109 (4 Pt 1), 1597-608.
9. Riedel, C. U.; Monk, I. R.; Casey, P. G.; Waidmann, M. S.; Gahan, C. G.; Hill, C., AgrD-dependent quorum sensing affects biofilm formation, invasion, virulence and global gene expression profiles in *Listeria monocytogenes*. *Mol Microbiol* 2009, 71 (5), 1177-89.
10. Rutherford, S. T.; Bassler, B. L., Bacterial quorum sensing: its role in virulence and possibilities for its control. *Cold Spring Harb Perspect Med* 2012, 2 (11). 11. Camilli, A.; Bassler, B. L., Bacterial small-molecule signaling pathways. *Science* 2006, 311 (5764), 1113-6.
12. Tal-Gan, Y.; Stacy, D. M.; Foegen, M. K.; Koenig, D. W.; Blackwell, H. E., Highly potent inhibitors of quorum sensing in *Staphylococcus aureus* revealed through a systematic synthetic study of the group-III autoinducing peptide. *J Am Chem Soc* 2013, 135 (21), 7869-82.
13. Mayville, P.; Ji, G.; Beavis, R.; Yang, H.; Goger, M.; Novick, R. P.; Muir, T. W., Structure-activity analysis of synthetic autoinducing thiolactone peptides from *Staphylococcus aureus* responsible for virulence. *Proc Natl Acad Sci USA* 1999, 96 (4), 1218-23.
14. Palmer, A. G.; Streng, E.; Blackwell, H. E., Attenuation of virulence in pathogenic bacteria using synthetic quorum-sensing modulators under native conditions on plant hosts. *ACS Chem Biol* 2011, 6 (12), 1348-56.
15. Mattmann, M. E.; Blackwell, H. E., Small molecules that modulate quorum sensing and control virulence in *Pseudomonas aeruginosa*. *J Org Chem* 2010, 75 (20), 6737-46.
16. Horswill, A. R.; Gordon, C. P., Structure-Activity-Relationship Studies of Small Molecule Modulators of the Staphylococcal Accessory Gene Regulator. *J Med Chem* 2019.
17. Rasko, D. A.; Sperandio, V., Anti-virulence strategies to combat bacteria-mediated disease. *Nat Rev Drug Discov* 2010, 9 (2), 117-28.
18. Dickey, S. W.; Cheung, G. Y. C.; Otto, M., Different drugs for bad bugs: antivirulence strategies in the age of antibiotic resistance. *Nat Rev Drug Discov* 2017, 16 (7), 457-471.
19. Thoendel, M.; Kavanaugh, J. S.; Flack, C. E.; Horswill, A. R., Peptide signaling in the *staphylococci*. *Chem Rev* 2011, 111 (1), 117-51.
20. Autret, N.; Raynaud, C.; Dubail, I.; Berche, P.; Charbit, A., Identification of the agr locus of *Listeria monocytogenes*: role in bacterial virulence. *Infect Immun* 2003, 71 (8), 4463-71.
21. Wang, B.; Muir, T. W., Regulation of Virulence in *Staphylococcus aureus*: Molecular Mechanisms and Remaining Puzzles. *Cell Chem Biol* 2016, 23 (2), 214-224.
22. Thoendel, M.; Horswill, A. R., Identification of *Staphylococcus aureus* AgrD residues required for autoinducing peptide biosynthesis. *J Biol Chem* 2009, 284 (33), 21828-38.
23. Wang, B.; Zhao, A.; Novick, R. P.; Muir, T. W., Key driving forces in the biosynthesis of autoinducing peptides required for staphylococcal virulence. *Proc Natl Acad Sci USA* 2015, 112 (34), 10679-84.
24. Wang, B.; Zhao, A.; Novick, R. P.; Muir, T. W., Activation and inhibition of the receptor histidine kinase AgrC occurs through opposite helical transduction motions. *Mol Cell* 2014, 53 (6), 929-40.
25. Vivant, A. L.; Garmyn, D.; Gal, L.; Piveteau, P., The Agr communication system provides a benefit to the populations of *Listeria monocytogenes* in soil. *Front Cell Infect Microbiol* 2014, 4, 160.
26. Vivant, A. L.; Garmyn, D.; Gal, L.; Hartmann, A.; Piveteau, P., Survival of *Listeria monocytogenes* in Soil Requires AgrA-Mediated Regulation. *Appl Environ Microbiol* 2015, 81 (15), 5073-84.
27. Freitag, N. E.; Rong, L.; Portnoy, D. A., Regulation of the prfA Transcriptional Activator of *Listeria monocytogenes*: Multiple Promoter Elements Contribute to Intracellular Growth and Cell-to-Cell Spread. *Infect Immun* 1993, 61 (6), 2537-2544.
28. de las Heras, A.; Cain, R. J.; Bielecka, M. K.; Vazquez-Boland, J. A., Regulation of *Listeria* virulence: PrfA master and commander. *Curr Opin Microbiol* 2011, 14 (2), 118-27.
29. Pinheiro, J.; Lisboa, J.; Pombinho, R.; Carvalho, F.; Carreaux, A.; Brito, C.; Pontinen, A.; Korkeala, H.; Dos Santos, N. M. S.; Morais-Cabral, J. H.; Sousa, S.; Cabanes, D., MouR controls the expression of the *Listeria monocytogenes* Agr system and mediates virulence. *Nucleic Acids Res* 2018, 46 (18), 9338-9352.
30. Chaudhuri, S.; Gantner, B. N.; Ye, R. D.; Cianciotto, N. P.; Freitag, N. E., The *Listeria monocytogenes* ChiA chitinase enhances virulence through suppression of host innate immunity. *mBio* 2013, 4 (2), e00617-12.
31. Paspaliari, D. K.; Mollerup, M. S.; Kallipolitis, B. H.; Ingmer, H.; Larsen, M. H., Chitinase expression in *Listeria monocytogenes* is positively regulated by the Agr system. *PLoS One* 2014, 9 (4), e95385.
32. Garmyn, D.; Augagneur, Y.; Gal, L.; Vivant, A. L.; Piveteau, P., *Listeria monocytogenes* differential transcriptome analysis reveals temperature-dependent Agr regulation and suggests overlaps with other regulons. *PLoS One* 2012, 7 (9), e43154.
33. Rieu, A.; Weidmann, S.; Garmyn, D.; Piveteau, P.; Guzzo, J., Agr system of *Listeria monocytogenes* EGD-e: role in adherence and differential expression pattern. *Appl Environ Microbiol* 2007, 73 (19), 6125-33.
34. Zetzmann, M.; Sanchez-Kopper, A.; Waidmann, M. S.; Blombach, B.; Riedel, C. U., Identification of the agr Peptide of *Listeria monocytogenes*. *Front Microbiol* 2016, 7, 989.
35. Todd, D. A.; Parlet, C. P.; Crosby, H. A.; Malone, C. L.; Heilmann, K. P.; Horswill, A. R.; Cech, N. B., Signal Biosynthesis Inhibition with Ambuic Acid as a Strategy To Target Antibiotic-Resistant Infections. *Antimicrob Agents Chemother* 2017, 61 (8). 36. Ji, G.; Beavis, R.; Novick, R. P., Bacterial interference caused by autoinducing peptide variants. *Science* 1997, 276 (5321), 2027-30.

37. Otto, M.; Echner, H.; Voelter, W.; Gotz, F., Pheromone cross-inhibition between *Staphylococcus aureus* and *Staphylococcus epidermidis*. *Infect Immun* 2001, 69 (3), 1957-60.
38. Brown, M. M.; Kwiecinski, J. M.; Cruz, L. M.; Shahbandi, A.; Todd, D. A.; Cech, N. B.; Horswill, A. R., Novel Peptide from Commensal *Staphylococcus simulans* Blocks Methicillin-Resistant *Staphylococcus aureus* Quorum Sensing and Protects Host Skin from Damage. *Antimicrob Agents Chemother* 2020, 64 (6).
39. Williams, M. R.; Costa, S. K.; Zaramela, L. S.; Khalil, S.; Todd, D. A.; Winter, H. L.; Sanford, J. A.; O'Neill, A. M.; Liggins, M. C.; Nakatsuji, T.; Cech, N. B.; Cheung, A. L.; Zengler, K.; Horswill, A. R.; Gallo, R. L., Quorum sensing between bacterial species on the skin protects against epidermal injury in atopic dermatitis. *Sci Transl Med* 2019, 11 (490).
40. Lyon, G. J.; Wright, J. S.; Muir, T. W.; Novick, R. P., Key determinants of receptor activation in the agr autoinducing peptides of *Staphylococcus aureus*. *Biochemistry* 2002, 41 (31), 10095-104.
41. Yang, T.; Tal-Gan, Y.; Paharik, A. E.; Horswill, A. R.; Blackwell, H. E., Structure-Function Analyses of a *Staphylococcus epidermidis* Autoinducing Peptide Reveals Motifs Critical for AgrC-type Receptor Modulation. *ACS Chem Biol* 2016, 11 (7), 1982-91.
42. Gordon, C. P.; Olson, S. D.; Lister, J. L.; Kavanaugh, J. S.; Horswill, A. R., Truncated Autoinducing Peptides as Antagonists of *Staphylococcus lugdunensis* Quorum Sensing. *J Med Chem* 2016, 59 (19), 8879-8888.
43. Chan, W. C.; Coyle, B. J.; Williams, P., Virulence regulation and quorum sensing in staphylococcal infections: competitive AgrC antagonists as quorum sensing inhibitors. *J Med Chem* 2004, 47 (19), 4633-41.
44. Wright, J. S., 3rd; Lyon, G. J.; George, E. A.; Muir, T. W.; Novick, R. P., Hydrophobic interactions drive ligand-receptor recognition for activation and inhibition of staphylococcal quorum sensing. *Proc Natl Acad Sci USA* 2004, 101 (46), 16168-73.
45. Tal-Gan, Y.; Ivancic, M.; Cornilescu, G.; Blackwell, H. E., Characterization of structural elements in native autoinducing peptides and non-native analogues that permit the differential modulation of AgrC-type quorum sensing receptors in *Staphylococcus aureus*. *Org Biomol Chem* 2016, 14 (1), 113-21.
46. Rodriguez-Lopez, P.; Rodriguez-Herrera, J. J.; Vazquez-Sanchez, D.; Lopez Cabo, M., Current Knowledge on *Listeria monocytogenes* Biofilms in Food-Related Environments: Incidence, Resistance to Biocides, Ecology and Biocontrol. *Foods* 2018, 7 (6).
47. Galie, S.; Garcia-Gutierrez, C.; Miguelez, E. M.; Villar, C. J.; Lombo, F., Biofilms in the Food Industry: Health Aspects and Control Methods. *Front Microbiol* 2018, 9, 898.
48. Rieu, A.; Briandet, R.; Habimana, O.; Garmyn, D.; Guzzo, J.; Piveteau, P., *Listeria monocytogenes* EGD-e biofilms: no mushrooms but a network of knitted chains. *Appl Environ Microbiol* 2008, 74 (14), 4491-7.
49. Zetzmann, M.; Bucur, F. I.; Crauwels, P.; Borda, D.; Nicolau, A. I.; Grigore-Gurgu, L.; Seibold, G. M.; Riedel, C. U., Characterization of the biofilm phenotype of a *Listeria monocytogenes* mutant deficient in agr peptide sensing. *Microbiologyopen* 2019, 8 (9), e00826.
50. Tal-Gan, Y.; Ivancic, M.; Cornilescu, G.; Yang, T.; Blackwell, H. E., Highly Stable, Amide-Bridged Autoinducing Peptide Analogues that Strongly Inhibit the AgrC Quorum Sensing Receptor in *Staphylococcus aureus*. *Angew Chem Int Ed Engl* 2016, 55 (31), 8913-7.
51. Zetzmann, M.; Okshevsky, M.; Endres, J.; Sedlag, A.; Caccia, N.; Auchter, M.; Waidmann, M. S.; Desvaux, M.; Meyer, R. L.; Riedel, C. U., DNase-Sensitive and -Resistant Modes of Biofilm Formation by *Listeria monocytogenes*. *Front Microbiol* 2015, 6, 1428.
52. Merritt, J. H.; Kadouri, D. E.; O'Toole, G. A., Growing and analyzing static biofilms. *Curr Protoc Microbiol* 2005, Chapter 1, Unit 1B 1.
53. Tal-Gan, Y.; Ivancic, M.; Cornilescu, G.; Blackwell, H. E., Characterization of structural elements in native autoinducing peptides and non-native analogues that permit the differential modulation of AgrC-type quorum sensing receptors in *Staphylococcus aureus*. *Org Biomol Chem* 2016, 14 (1), 113-21.
54. Blanco-Canosa, J. B.; Dawson, P. E., An efficient Fmoc-SPPS approach for the generation of thioester peptide precursors for use in native chemical ligation. *Angew Chem Int Ed Engl* 2008, 47 (36), 6851-5.
55. Tal-Gan, Y.; Ivancic, M.; Cornilescu, G.; Yang, T.; Blackwell, H. E., Highly Stable, Amide-Bridged Autoinducing Peptide Analogues that Strongly Inhibit the AgrC Quorum Sensing Receptor in *Staphylococcus aureus*. *Angew Chem Int Ed Engl* 2016, 55 (31), 8913-7.
56. Ji, G.; Beavis, R.; Novick, R. P., Bacterial interference caused by autoinducing peptide variants. *Science* 1997, 276 (5321), 2027-30.
57. Otto, M.; Echner, H.; Voelter, W.; Gotz, F., Pheromone cross-inhibition between *Staphylococcus aureus* and *Staphylococcus epidermidis*. *Infect Immun* 2001, 69 (3), 1957-60.
58. Brown, M. M.; Kwiecinski, J. M.; Cruz, L. M.; Shahbandi, A.; Todd, D. A.; Cech, N. B.; Horswill, A. R., Novel Peptide from Commensal *Staphylococcus simulans* Blocks Methicillin-Resistant *Staphylococcus aureus* Quorum Sensing and Protects Host Skin from Damage. *Antimicrob Agents Chemother* 2020, 64 (6).
59. Williams, M. R.; Costa, S. K.; Zaramela, L. S.; Khalil, S.; Todd, D. A.; Winter, H. L.; Sanford, J. A.; O'Neill, A. M.; Liggins, M. C.; Nakatsuji, T.; Cech, N. B.; Cheung, A. L.; Zengler, K.; Horswill, A. R.; Gallo, R. L., Quorum sensing between bacterial species on the skin protects against epidermal injury in atopic dermatitis. *Sci Transl Med* 2019, 11 (490).
60. Thoendel, M.; Kavanaugh, J. S.; Flack, C. E.; Horswill, A. R., Peptide signaling in the staphylococci. *Chem Rev* 2011, 111 (1), 117-51.
61. Garmyn, D.; Gal, L.; Lemaitre, J. P.; Hartmann, A.; Piveteau, P., Communication and autoinduction in the species *Listeria monocytogenes*: A central role for the agr system. *Commun Integr Biol* 2009, 2 (4), 371-4.
62. Orsi, R. H.; Wiedmann, M., Characteristics and distribution of *Listeria* spp., including *Listeria* species newly described since 2009. *Appl Microbiol Biotechnol* 2016, 100 (12), 5273-87.
63. Schardt, J.; Jones, G.; Muller-Herbst, S.; Schauer, K.; D'Orazio, S. E. F.; Fuchs, T. M., Comparison between *Listeria sensu stricto* and *Listeria sensu lato* strains identifies novel determinants involved in infection. *Sci Rep* 2017, 7 (1), 17821.
64. Yang, T.; Tal-Gan, Y.; Paharik, A. E.; Horswill, A. R.; Blackwell, H. E., Structure-Function Analyses of a *Staphylococcus epidermidis* Autoinducing Peptide Reveals Motifs Critical for AgrC-type Receptor Modulation. *ACS Chem Biol* 2016, 11 (7), 1982-91.

65. Tal-Gan, Y.; Stacy, D. M.; Foegen, M. K.; Koenig, D. W.; Blackwell, H. E., Highly potent inhibitors of quorum sensing in *Staphylococcus aureus* revealed through a systematic synthetic study of the group-III autoinducing peptide. *J Am Chem Soc* 2013, 135 (21), 7869-82.

66. Horswill, A. R.; Gordon, C. P., Structure-Activity-Relationship Studies of Small Molecule Modulators of the Staphylococcal Accessory Gene Regulator. *J Med Chem* 2019.

EQUIVALENTS

While certain embodiments have been illustrated and described, a person with ordinary skill in the art, after reading the foregoing specification, can effect changes, substitutions of equivalents and other types of alterations to the conjugates and micelles of the present technology or derivatives, prodrugs, or pharmaceutical compositions thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, conjugates, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound of Formula I

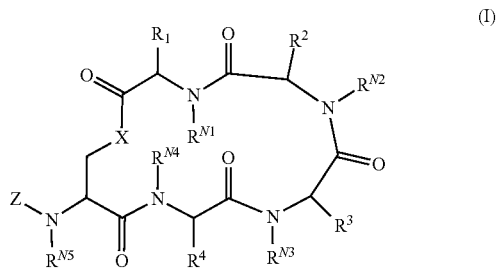

stereoisomers thereof, and/or salts thereof,
wherein
X is S, O, NH, NR, CH$_2$ or CH, provided that the CH forms a double bond with an adjacent carbon;
Z is R$^T$, R$^T$—C(O), an amino acid residue, or a peptide of 2-10 amino acid residues, wherein Z is optionally attached to a solid substrate;
R is an unsubstituted C$_{1-6}$ alkyl group;
R$^{N1}$, R$^{N2}$, R$^{N3}$, R$^{N4}$, and R$^{N5}$ are each independently H or CH$_3$;
R$^1$ is a substituted or unsubstituted alkyl, heteroalkyl, aryl, aralkyl, heteroaryl, or heteroaralkyl group;
R$^2$ is a substituted or unsubstituted alkyl, heteroalkyl, aryl, aralkyl, heteroaryl, or heteroaralkyl group;
R$^3$ is a substituted or unsubstituted alkyl or heteroalkyl group;

R$^4$ is a substituted or unsubstituted alkyl, heteroalkyl, aryl, aralkyl, heteroaryl, or heteroaralkyl group; and R$^T$ is hydrogen, PEG, a substituted or unsubstituted alkyl, heteroalkyl aryl, or aralkyl group, or a substituted or unsubstituted alkoxy, aryloxy, or aralkoxy group;

provided that the compound is not A-(C-F-M-F-V) (SEQ ID NO: 1) and is not K-A(C-F-M-F-V) (SEQ ID NO: 2).

B. The compound of Paragraph A wherein

R$^1$ is an unsubstituted C$_{1-6}$ alkyl group, or a substituted or unsubstituted phenyl or a benzyl group;

R$^2$ and R$^4$ are independently selected from an unsubstituted C$_{1-6}$ alkyl group, or a substituted or unsubstituted phenyl, benzyl, indolyl, or indolylmethyl group;

R$_3$ is an unsubstituted C$_{1-6}$ alkyl group, a C$_{1-6}$ alkylenethioalkyl group, a C$_{1-6}$ alkylene-oxyalkyl group, or a C$_{1-6}$ hydroxyalkyl group;

R$^T$ is hydrogen or a substituted or unsubstituted C$_{1-6}$ alkyl group; or, when Z is R$^T$—C(O), R$^T$ is —OR$^5$, wherein R$^5$ is a substituted or unsubstituted C$_{1-6}$ alkyl, benzyl or fluorenylmethyl group; and each substituent present on any substituted group is independently selected from halogen, hydroxyl, unsubstituted C$_{1-6}$ alkyl, amino-substituted C$_{1-6}$ alkyl, C$_{1-6}$ alkoxy, amino, C$_{1-6}$ alkylamino, di-C$_{1-6}$-alkyl amino, C$_{1-6}$ haloalkyl, C$_{1-6}$ haloalkoxy, thiol, C$_{1-6}$ alkylthio, —CO$_2$R$^a$ where R$^a$ is hydrogen or an unsubstituted C$_{1-6}$ alkyl, —COR', where R' is H or an unsubstituted C$_{1-6}$ alkyl group, —CO—NR"$_2$, where each R" is independently hydrogen or C$_{1-6}$ alkyl, azido, nitro, cyano, isocyano, thiocyano, isothiocyano, cyanate, isocyanate, thiocyanate, or isothiocyanate groups;

provided that the compound is not A-(C-F-M-F-V) and is not K-A(C-F-M-F-V).

C. The compound of Paragraph A or Paragraph B, wherein X is S.

D. The compound of Paragraph A or Paragraph B, wherein X is O.

E. The compound of Paragraph A or Paragraph B, wherein X is NH.

F. The compound of Paragraph A or Paragraph B, wherein X is NCH$_3$.

G. The compound of any preceding Paragraph, wherein Z is an amino acid residue or a peptide of 2-10 amino acid residues.

H. The compound of Paragraph G, wherein Z is an amino acid residue or a dipeptide.

I. The compound of Paragraph H, wherein Z is selected from an alanine, valine, or lysine residue, or lysine-alanine dipeptide.

J. The compound of any one of Paragraphs A-F, wherein Z is R$^T$ or R$^T$—C(O).

K. The compound of Paragraph J, wherein R$^T$ is hydrogen or a methyl group.

L. The compound of any preceding Paragraph wherein each of RN$^1$, R$^{N2}$, R$^{N3}$, R$^{N4}$, and R$^{N5}$ is H.

M. The compound of any preceding Paragraph, wherein R$^1$ is a substituted or unsubstituted C$_{1-6}$ alkyl group.

N. The compound of any preceding Paragraph, wherein R$^1$ is a substituted or unsubstituted C$_{3-6}$ branched alkyl group.

O. The compound of any preceding Paragraph, wherein R$^2$ is a substituted or unsubstituted C$_{3-6}$ alkyl group, or an aralkyl or heteroaralkyl group.

P. The compound of Paragraph O, wherein R$^2$ is substituted or unsubstituted benzyl.

Q. The compound of Paragraph O, wherein R$^2$ is benzyl, para-hydroxy benzyl, imidazolylmethyl, or indolylmethyl.

R. The compound of any preceding Paragraph, wherein R$^3$ is an unsubstituted C$_{1-6}$ alkyl or C$_{2-6}$ heteroalkyl group.

S. The compound of Paragraph R, wherein R$^4$ is a substituted or unsubstituted C$_{3-6}$ alkyl group, or an aralkyl or heteroaralkyl group.

T. The compound of Paragraph S, wherein R$^4$ is benzyl, para-hydroxy benzyl, imidazolylmethyl, or indolylmethyl.

U. The compound of any preceding Paragraph wherein the stereochemistry of all amino acid residues is L.

V. The compound of any one of Paragraphs A-U, wherein the stereochemistry of one or more amino acid residues is D.

W. The compound of Paragraph V, wherein the stereochemistry of the amino acid residue at position 5 of Formula (I) is D.

X. The compound of Paragraph V or Paragraph W, wherein the stereochemistry of the amino acid residue at position 3 of Formula (I) is D.

Y. The compound of any preceding Paragraph wherein each substituent present is independently selected from halogen, hydroxyl, unsubstituted C$_{1-6}$ alkyl, amino-substituted C$_{1-6}$ alkyl, C$_{1-6}$ alkoxy, amino, C$_{1-6}$ alkylamino, di-C$_{1-6}$-alkyl amino, C$_{1-6}$ haloalkyl, C$_{1-6}$ haloalkoxy, thiol, C$_{1-6}$ alkylthio, —CO$_2$R$^a$ where R$^a$ is hydrogen or an unsubstituted C$_{1-6}$ alkyl —COR', where R' is H or an unsubstituted C$_{1-6}$ alkyl group, —CO—NR"$_2$, where each R" is independently hydrogen or C$_{1-6}$ alkyl, azido, nitro, cyano, isocyano, thiocyano, isothiocyano, cyanate, isocyanate, thiocyanate, or isothiocyanate groups.

Z. The compound of Paragraph A selected from the group consisting of A-(C-F-dM-F-V), V-(C-F-M-F-V) (SEQ ID NO: 3), K-A-(dC-F-dM-F-V), and K-(dC-F-dM-F-V).

AA. A composition comprising a compound of any one of Paragraphs A-Z and a carrier and/or excipient.

BB. The composition of Paragraph AA comprising an amount of the compound effective for inhibiting *Listeria monocytogenes* virulence, wherein the carrier and/or excipients are pharmaceutically acceptable, and the composition is a pharmaceutical composition.

CC. The composition of Paragraph AA, comprising an amount of the compound effective for inhibiting *Listeria monocytogenes* biofilm formation on a surface and the composition is a disinfectant.

DD. The composition of any one of Paragraphs AA-CC, wherein the compound is selected from K-A-(dC-F-dM-F-V), and K-(dC-F-dM-F-V).

EE. A method for modulating quorum sensing in *Listeria monocytogenes* comprising contacting *Listeria monocytogenes* with an effective amount of a compound of any one of Paragraphs A-Z.

FF. The method of Paragraph EE, wherein the compound is selected from A-(C-F-dM-F-V), V-(C-F-M-F-V) (SEQ ID NO: 3), and quorum sensing by *Listeria monocytogenes* is activated.

GG. The method of Paragraph EE, wherein the compound is selected from K-A-(dC-F-dM-F-V), and K-(dC-F-dM-F-V), and quorum sensing by *Listeria monocytogenes* is inhibited.

HH. A method for reducing *Listeria monocytogenes* virulence comprising contacting the *Listeria monocytogenes* with an effective amount of a compound of any one of Paragraphs A-Z.

II. The method of Paragraph HH, wherein the compound is selected from one in which the stereochemistry of the amino acid residue at position 3 or positions 3 and 5 of Formula (I) is D.

JJ. The method of Paragraph HH or Paragraph II, wherein the compound is selected from K-A-(dC-F-dM-F-V) and/or K-(dC-F-dM-F-V).

KK. A method of inhibiting biofilm formation or growth by *Listeria monocytogenes* on a surface comprising contacting the *Listeria monocytogenes* with an effective amount of a compound of any one of Paragraphs A-Z.

LL. The method of Paragraph KK, wherein the compound is selected from one in which the stereochemistry of the amino acid residue at position 3 or position 3 and 5 of Formula (I) is D.

MM. The method of Paragraph KK or Paragraph LL, wherein the compound is selected from K-A-(dC-F-dM-F-V) and/or K-(dC-F-dM-F-V).

NN. The method any one of Paragraphs KK-MM, further comprising applying the effective amount of the compound to the surface.

OO. The method of Paragraph NN, wherein the surface is a food surface, a food-preparation surface, or a food packaging surface.

PP. A method of treating a *Listeria monocytogenes* infection in a subject comprising administering to the subject an effective amount of a compound of any one of Paragraphs A-Z to the subject.

QQ. The method of Paragraph PP, wherein the subject is a non-human animal.

RR. The method of Paragraph QQ, wherein the subject is selected from the group consisting of cattle, sheep, buffalo and goats.

SS. The method of Paragraph PP, wherein the subject is human.

TT. The method of any one of Paragraphs PP-SS, wherein the compound is selected from one in which the stereochemistry of the amino acid residue at position 3 or position 3 and 5 of Formula (I) is D.

UU. The method of Paragraph TT, wherein the compound is selected from K-A-(dC-F-dM-F-V) and/or K-(dC-F-dM-F-V).

What is claimed is:

1. A compound of Formula I $$\text{(I)}$$

stereoisomers thereof, and/or salts thereof,
wherein
X is S;
Z is a lysine residue or a lysine-lysine dipeptide, wherein Z is optionally attached to a solid substrate;
$R^{N1}$, $R^{N2}$, $R^{N3}$, $R^{N4}$, and $R^{N5}$ are each independently H;
$R^1$ is an unsubstituted $C_{1-6}$ alkyl group;
$R^2$ is benzyl, para-hydroxy benzyl, imidazolylmethyl, or indolylmethyl;
$R^3$ is an unsubstituted $C_{2-6}$ heteroalkyl group;
$R^4$ is a benzyl, para-hydroxy benzyl, imidazolylmethyl, or indolylmethyl group; and
the stereochemistry of the amino acid residue at positions 3 and 5 of Formula (I) is D.

2. The compound of claim 1, wherein the compound is K-(dC-F-dM-F-V).

3. A composition comprising a compound of claim 1 and a carrier and/or excipient.

4. The composition of claim 3 comprising an amount of the compound effective for inhibiting *Listeria monocytogenes* virulence, wherein the carrier and/or excipients are pharmaceutically acceptable, and the composition is a pharmaceutical composition.

5. The composition of claim 3, comprising an amount of the compound effective for inhibiting *Listeria monocytogenes* biofilm formation on a surface and the composition is a disinfectant.

6. The composition of claim 3, wherein the compound is K-(dC-F-dM-F-V).

7. A method for modulating quorum sensing in *Listeria monocytogenes* comprising contacting *Listeria monocytogenes* with an effective amount of a compound of claim 1.

8. The method of claim 7, wherein the compound is K-(dC-F-dM-F-V), and quorum sensing by *Listeria monocytogenes* is inhibited.

9. A method for reducing *Listeria monocytogenes* virulence comprising contacting the *Listeria monocytogenes* with an effective amount of a compound of claim 1.

10. The method of claim 9, wherein the compound is K-(dC-F-dM-F-V).

11. A method of inhibiting biofilm formation or growth by *Listeria monocytogenes* on a surface comprising contacting the *Listeria monocytogenes* with an effective amount of a compound of claim 1.

12. The method of claim 11, wherein the compound is selected from K-(dC-F-dM-F-V).

13. A method of treating a *Listeria monocytogenes* infection in a subject comprising administering to the subject an effective amount of a compound of claim 1 to the subject.

14. The method of claim 13, wherein the subject is human.

15. The method of claim 14, wherein the compound is K-(dC-F-dM-F-V).

* * * * *

SEQUENCE LISTING

```
<160> NUMBER OF SEQ ID NOS: 48

<210> SEQ ID NO 1
<211> LENGTH: 6
<212> TYPE: PRT
<213> ORGANISM: Listeria monocytogenes

<400> SEQUENCE: 1

Ala Cys Phe Met Phe Val
1               5

<210> SEQ ID NO 2
<211> LENGTH: 7
<212> TYPE: PRT
<213> ORGANISM: Listeria monocytogenes

<400> SEQUENCE: 2

Lys Ala Cys Phe Met Phe Val
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Cys Phe Met Phe Val
1               5

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aatccatgcc aacccgttcc atgt                                          24

<210> SEQ ID NO 5
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
acgcatcgtg gccggcatc                                                  19

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Cys Ser Met Phe Val
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Cys Phe Met Phe Ala
1               5

<210> SEQ ID NO 8
<211> LENGTH: 8
<212> TYPE: PRT
<213> ORGANISM: Staphylococcus aureus

<400> SEQUENCE: 8

Tyr Ser Thr Cys Asp Phe Ile Met
1               5

<210> SEQ ID NO 9
<211> LENGTH: 9
<212> TYPE: PRT
<213> ORGANISM: Staphylococcus aureus

<400> SEQUENCE: 9

Gly Val Asn Ala Cys Ser Ser Leu Phe
1               5

<210> SEQ ID NO 10
<211> LENGTH: 7
<212> TYPE: PRT
<213> ORGANISM: Staphylococcus aureus

<400> SEQUENCE: 10

Ile Asn Cys Asp Phe Leu Leu
1               5

<210> SEQ ID NO 11
<211> LENGTH: 8
<212> TYPE: PRT
<213> ORGANISM: Staphylococcus aureus

<400> SEQUENCE: 11
```

```
Tyr Ser Thr Cys Tyr Phe Ile Met
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Asn Cys Ala Phe Leu Leu
1               5

<210> SEQ ID NO 13
<211> LENGTH: 8
<212> TYPE: PRT
<213> ORGANISM: Staphylococcus epidermidis

<400> SEQUENCE: 13

Asp Ser Val Cys Ala Ser Tyr Phe
1               5

<210> SEQ ID NO 14
<211> LENGTH: 12
<212> TYPE: PRT
<213> ORGANISM: Staphylococcus epidermidis

<400> SEQUENCE: 14

Asn Ala Ser Lys Tyr Asn Pro Cys Ser Asn Tyr Leu
1               5                   10

<210> SEQ ID NO 15
<211> LENGTH: 12
<212> TYPE: PRT
<213> ORGANISM: Staphylococcus epidermidis

<400> SEQUENCE: 15

Asn Ala Ala Lys Tyr Asn Pro Cys Ala Ser Tyr Leu
1               5                   10

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Ser Val Cys Ala Ala Tyr Phe
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ser Ala Cys Ala Ala Tyr Phe
1               5
```

```
<210> SEQ ID NO 18
<211> LENGTH: 5
<212> TYPE: PRT
<213> ORGANISM: Listeria grandensis

<400> SEQUENCE: 18

Cys Val Gly Phe Val
1               5

<210> SEQ ID NO 19
<211> LENGTH: 6
<212> TYPE: PRT
<213> ORGANISM: Listeria grayi

<400> SEQUENCE: 19

Ala Cys Ser Met Phe Ala
1               5

<210> SEQ ID NO 20
<211> LENGTH: 6
<212> TYPE: PRT
<213> ORGANISM: Listeria kieliensis

<400> SEQUENCE: 20

Ser Cys Val Gly Leu Ser
1               5

<210> SEQ ID NO 21
<211> LENGTH: 6
<212> TYPE: PRT
<213> ORGANISM: Listeria newyorkensis

<400> SEQUENCE: 21

Ser Cys Phe Leu Ile Phe
1               5

<210> SEQ ID NO 22
<211> LENGTH: 6
<212> TYPE: PRT
<213> ORGANISM: Listeria weihenstephanensis

<400> SEQUENCE: 22

Ser Cys Val Leu His Leu
1               5

<210> SEQ ID NO 23
<211> LENGTH: 5
<212> TYPE: PRT
<213> ORGANISM: Listeria monocytogenes

<400> SEQUENCE: 23

Cys Phe Met Phe Val
1               5

<210> SEQ ID NO 24
<211> LENGTH: 5
<212> TYPE: PRT
<213> ORGANISM: Listeria monocytogenes

<400> SEQUENCE: 24

Cys Phe Met Phe Val
1               5

<210> SEQ ID NO 25
<211> LENGTH: 8
```

```
<212> TYPE: PRT
<213> ORGANISM: Listeria monocytogenes

<400> SEQUENCE: 25

Ser Lys Ala Cys Phe Met Phe Val
1               5

<210> SEQ ID NO 26
<211> LENGTH: 9
<212> TYPE: PRT
<213> ORGANISM: Listeria monocytogenes

<400> SEQUENCE: 26

Met Ser Lys Ala Cys Phe Met Phe Val
1               5

<210> SEQ ID NO 27
<211> LENGTH: 10
<212> TYPE: PRT
<213> ORGANISM: Listeria monocytogenes

<400> SEQUENCE: 27

Ser Met Ser Lys Ala Cys Phe Met Phe Val
1               5                   10

<210> SEQ ID NO 28
<211> LENGTH: 11
<212> TYPE: PRT
<213> ORGANISM: Listeria monocytogenes

<400> SEQUENCE: 28

Ser Ser Met Ser Lys Ala Cys Phe Met Phe Val
1               5                   10

<210> SEQ ID NO 29
<211> LENGTH: 12
<212> TYPE: PRT
<213> ORGANISM: Listeria monocytogenes

<400> SEQUENCE: 29

Asp Ser Ser Met Ser Lys Ala Cys Phe Met Phe Val
1               5                   10

<210> SEQ ID NO 30
<211> LENGTH: 13
<212> TYPE: PRT
<213> ORGANISM: Listeria monocytogenes

<400> SEQUENCE: 30

Ala Asp Ser Ser Met Ser Lys Ala Cys Phe Met Phe Val
1               5                   10

<210> SEQ ID NO 31
<211> LENGTH: 14
<212> TYPE: PRT
<213> ORGANISM: Listeria monocytogenes

<400> SEQUENCE: 31

Val Ala Asp Ser Ser Met Ser Lys Ala Cys Phe Met Phe Val
1               5                   10

<210> SEQ ID NO 32
<211> LENGTH: 15
<212> TYPE: PRT
<213> ORGANISM: Listeria monocytogenes
```

<400> SEQUENCE: 32

Lys Val Ala Asp Ser Ser Met Ser Lys Ala Cys Phe Met Phe Val
1               5                   10                  15

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Cys Ala Met Phe Val
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Cys Phe Ala Phe Val
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Cys Phe Met Ala Val
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Pro Cys Phe Met Phe Val
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Cys Phe Met Phe Val
1               5

<210> SEQ ID NO 38
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Cys Phe Met Phe Val
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N(alpha)-Fmoc-N(beta)-4-Mtt-diaminopropionic
      acid

<400> SEQUENCE: 39

Ala Xaa Phe Met Phe Val
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Cys Tyr Met Phe Val
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Cys Leu Met Phe Val
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Cys His Met Phe Val
1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 43

Ala Cys Trp Met Phe Val
1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Cys Phe Met Tyr Val
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Cys Phe Met Leu Val
1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Cys Phe Met His Val
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Cys Phe Met Trp Val
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Lys Lys Cys Phe Met Phe Val
1               5
```